(12) United States Patent
Simanzhenkov et al.

(10) Patent No.: US 11,998,895 B2
(45) Date of Patent: Jun. 4, 2024

(54) OXIDATIVE DEHYDROGENATION CATALYST COMPOSITIONS

(71) Applicant: NOVA Chemicals (International) S.A., Fribourg (CH)

(72) Inventors: Vasily Simanzhenkov, Calgary (CA); Xiaoliang Gao, Calgary (CA); Marie Barnes, Calgary (CA); David Sullivan, Calgary (CA); Yoonhee Kim, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 0 days.

(21) Appl. No.: 17/860,143

(22) Filed: Jul. 8, 2022

(65) Prior Publication Data
US 2023/0278013 A1 Sep. 7, 2023

Related U.S. Application Data

(62) Division of application No. 16/528,795, filed on Aug. 1, 2019, now Pat. No. 11,413,604.
(Continued)

(51) Int. Cl.
*B01J 21/04* (2006.01)
*B01J 23/00* (2006.01)
(Continued)

(52) U.S. Cl.
CPC .............. *B01J 23/28* (2013.01); *B01J 21/04* (2013.01); *B01J 23/002* (2013.01); *B01J 37/08* (2013.01);
(Continued)

(58) Field of Classification Search
CPC . B01J 21/04; B01J 23/002; B01J 23/28; B01J 37/08; B01J 2523/00; B01J 2523/55;
(Continued)

(56) References Cited

U.S. PATENT DOCUMENTS 8,846,996 B2 9/2014 Kustov et al.
10,350,582 B2 7/2019 Simanzhenkov et al.
(Continued)

FOREIGN PATENT DOCUMENTS

CA 2 655 841 A1 8/2010
DE 198 36 359 A1 3/1999
(Continued)

OTHER PUBLICATIONS

CN Office Action in Chinese Appln. No. 201980051484.3, dated Jun. 14, 2022, 21 pages (with English translation).
(Continued)

*Primary Examiner* — Jun Li
(74) *Attorney, Agent, or Firm* — Thomas J. Styslinger

(57) ABSTRACT

Provided in this disclosure are catalyst compositions. The catalyst compositions include an oxidative dehydrogenation catalyst that includes a mixed metal oxide having the empirical formula:

$$Mo_{1.0}V_{0.12-0.49}Te_{0.05-0.17}Nb_{0.10-0.20}Al_cO_d$$

wherein c is from 0 to 2.0 and d is a number to satisfy the valence of the oxide. The compositions are at least 40 wt. % amorphous as measured by XRD. The disclosure also provides methods of making the compositions.

17 Claims, 3 Drawing Sheets

Related U.S. Application Data

(60) Provisional application No. 62/714,289, filed on Aug. 3, 2018.

(51) Int. Cl.
  B01J 23/28 (2006.01)
  B01J 37/08 (2006.01)
  C07C 5/48 (2006.01)

(52) U.S. Cl.
  CPC .............. *C07C 5/48* (2013.01); *B01J 2523/55* (2013.01); *B01J 2523/56* (2013.01); *B01J 2523/64* (2013.01); *B01J 2523/68* (2013.01); *C07C 2521/04* (2013.01); *C07C 2523/20* (2013.01); *C07C 2523/22* (2013.01); *C07C 2523/28* (2013.01); *C07C 2523/32* (2013.01)

(58) Field of Classification Search
  CPC ................ B01J 2523/56; B01J 2523/64; B01J 2523/68; B01J 2523/31
  See application file for complete search history.

(56) References Cited

U.S. PATENT DOCUMENTS

| | | | |
|---|---|---|---|
| 10,406,517 B2 | 9/2019 | Simanzhenkov et al. | |
| 10,576,461 B2 | 3/2020 | Simanzhenkov et al. | |
| 10,589,258 B2 | 3/2020 | Simanzhenkov et al. | |
| 10,661,256 B2 * | 5/2020 | Kim .................... B01J 37/0018 | |
| 11,014,072 B2 | 5/2021 | Simanzhenkov et al. | |
| 2003/0208085 A1 * | 11/2003 | Gaffney .................. B01J 23/28 | 558/321 |
| 2006/0004228 A1 | 1/2006 | Hazin | |
| 2006/0052635 A1 | 3/2006 | Rosen | |
| 2010/0255986 A1 | 10/2010 | Gaffney et al. | |
| 2010/0256432 A1 | 10/2010 | Arnold et al. | |
| 2013/0261361 A1 * | 10/2013 | Blommel .................. B01J 23/72 | 585/322 |
| 2014/0114109 A1 * | 4/2014 | Sanchez Valente ...... C07C 5/48 | 585/658 |
| 2015/0119622 A1 | 4/2015 | De Rooij et al. | |
| 2016/0207035 A1 | 7/2016 | Zander et al. | |
| 2017/0050178 A1 | 2/2017 | Simanzhenkov et al. | |
| 2017/0233312 A1 | 8/2017 | Hossain et al. | |
| 2018/0104675 A1 | 4/2018 | Simanzhenkov et al. | |
| 2019/0039050 A1 | 2/2019 | Gao et al. | |
| 2019/0039053 A1 | 2/2019 | Kim et al. | |
| 2019/0240647 A1 | 4/2019 | Gao et al. | |
| 2019/0291080 A1 | 9/2019 | Simanzhenkov et al. | |

FOREIGN PATENT DOCUMENTS

| | | | | |
|---|---|---|---|---|
| EP | 1 080 784 A1 | 3/2001 | | |
| EP | 1 574 253 A2 | 9/2005 | | |
| ES | 2428442 A2 * | 11/2013 | ............ | B01J 23/002 |
| WO | 2008/068332 A1 | 6/2008 | | |
| WO | WO 2009106474 | 9/2009 | | |

OTHER PUBLICATIONS

JP Office Action in Japanese Appln. No. 2021-505860, dated May 19, 2023, 13 pages (with English translation).

PCT International Search Report and Written Opinion in International Appln. No. PCT/IB2019/056577, mailed on Nov. 7, 2019, 14 pages.

Chu, Bozhao; Truter, Lara; Nijhuis, T.A. and Cheng, Yi; Performance of phase-pure M1 MoVNbTeOx catalysts by hydrothermal synthesis with different post-treatments for the oxidative dehydrogenation of ethane; Applied Catalysis A, General 438 (2015), pp. 99-106.

* cited by examiner

OXIDATIVE DEHYDROGENATION CATALYST COMPOSITIONS

CROSS REFERENCE TO RELATED APPLICATIONS

This application is a divisional of U.S. application Ser. No. 16/528,795 which was filed on Aug. 1, 2019, which claims the benefit of the filing date of U.S. Provisional Application No. 62/714,289, which was filed on Aug. 3, 2018. The contents of these applications are incorporated by reference in their entirety as part of this application.

TECHNICAL FIELD

The present disclosure relates to catalyst compositions for the oxidative dehydrogenation of alkanes.

BACKGROUND

Conversion of alkanes to olefins can be achieved in a number of ways. The most widely practiced method is thermal cracking technology, where alkanes are exposed to temperatures of at least 700° C. for very short time periods, in the order of milliseconds to a few seconds, promoting the loss of hydrogen and subsequent formation of one or more unsaturated bonds characteristic of olefins. However, the current thermal cracking processes are not only cost intensive to build and operate but also energy intensive due to the substantial heat requirement for the endothermic cracking reactions. Also, significant amounts of $CO_2$ are produced from the operation of cracking furnaces.

Alternatively, conversion of paraffins can be accomplished using an oxidative dehydrogenation process where a stream of one or more alkanes are passed over an oxidative dehydrogenation catalyst, in the presence of oxygen or an oxygen containing gas, at temperatures from about 300° C. to 750° C. The advantages of catalytic oxidative dehydrogenation over steam cracking are that it provides higher ethane conversion and higher ethylene selectivity while using lower reaction temperatures. However, developing catalysts is made difficult because olefins are more reactive than the alkanes they are derived from, creating the potential for further oxidation to unwanted byproducts. It is therefore desirable to use catalysts that are more selective for oxidation of alkanes than olefins.

SUMMARY

Provided in this disclosure is a catalyst composition. The catalyst composition includes an oxidative dehydrogenation catalyst that includes a mixed metal oxide having the empirical formula:

$$Mo_{1.0}V_{0.12-0.49}Te_{0.05-0.25}Nb_{0.10-0.20}Al_cO_d$$

wherein c is from 0 to 2.0 and d is a number to satisfy the valence of the oxide. The composition is at least 40 wt. % amorphous.

In some embodiments, the composition is from 60 wt. % to 80 wt. % amorphous.

In some embodiments, the catalyst composition further includes an adjuvant. In some embodiments, the adjuvant is present in an amount from about 30 wt. % to about 90 wt. % of the catalyst composition. For example, the adjuvant can be present in an amount of about 60 wt. % of the catalyst composition.

In some embodiments, the oxidative dehydrogenation catalyst is present in an amount from about 10 wt. % to about 70 wt. % of the catalyst composition. For example, the oxidative dehydrogenation catalyst can be present in an amount of about 40 wt. % of the catalyst composition.

In some embodiments, the adjuvant is chosen from a support, a binder, an agglomerating agent, a promoter, an agent capable of at least partially reacting with the oxidative dehydrogenation catalyst, or a combination thereof. In some embodiments, the adjuvant includes an agent capable of at least partially reacting with the oxidative dehydrogenation catalyst.

In some embodiments, the mixed metal oxide has the empirical formula:

$$Mo_{1.0}V_{0.12-0.49}Te_{0.05-0.17}Nb_{0.10-0.20}Al_cO_d$$

wherein c is 0.01 to 2.0 and d is a number to satisfy the valence of the oxide.

In some embodiments, the adjuvant includes an alumina. The alumina can be chosen from an aluminum oxide, an alumina monohydrate, an alumina trihydrate, an alumina-silica, a bauxite, a calcined alumina, a transition alumina, a calcined hydrotalcite, or a combination thereof. In some embodiments, the alumina includes an alumina chosen from a gibbsite, a bayerite, a boehmite, or a combination thereof. In some embodiments, the alumina includes a boehmite. In some embodiments, the adjuvant includes a pseudoboehmite. In some embodiments, the alumina is present in an amount from about 30 wt. % to about 90 wt. % of the catalyst composition. In some embodiments, the alumina is present in an amount of about 60 wt. % of the catalyst composition. In some embodiments, the alumina is present in an amount of about 55 wt. % of the catalyst composition.

In some embodiments, the catalyst composition is characterized by having XRD diffraction peaks (2θ degrees) at least at 22±0.2, 27±0.2, 28.0±0.2, and 28.3±0.2, wherein the XRD is obtained using CuKα radiation.

In some embodiments, the catalyst composition has a 35% conversion temperature from about 340° C. to about 390° C. For example, the catalyst composition can have a 35% conversion temperature from about 350° C. to about 370° C.

In some embodiments, the catalyst composition has a selectivity to ethylene of greater than about 90%. In some embodiments, the catalyst composition has a selectivity to ethylene of greater than about 93%.

In some embodiments, the catalyst composition has a 35% conversion temperature from about 350° C. to about 390° C. and a selectivity to ethylene of greater than about 90%. In some embodiments, the catalyst composition has a 35% conversion temperature from about 360° C. to about 370° C. and a selectivity to ethylene of greater than about 93%.

Also provided in this disclosure is a catalyst composition that includes a boehmite and an oxidative dehydrogenation catalyst. The oxidative dehydrogenation catalyst includes a mixed metal oxide having the empirical formula:

$$Mo_{1.0}V_{0.12-0.49}Te_{0.05-0.25}Nb_{0.10-0.20}Al_{0-2.0}O_d$$

wherein d is a number to satisfy the valence of the oxide. The boehmite is present in an amount from about 50 wt. % to about 70 wt. % of the catalyst composition. The oxidative dehydrogenation catalyst is present in an amount from about 30 wt. % to about 50 wt. % of the catalyst composition. Further, the catalyst composition is about 60 wt. % to about 80 wt. % amorphous.

In some embodiments, the catalyst composition has a 35% conversion temperature from about 350° C. to about 370° C. and a selectivity to ethylene of greater than about 90%.

Further provided in this disclosure is a catalyst composition that includes an alumina and an oxidative dehydrogenation catalyst. The oxidative dehydrogenation catalyst includes a mixed metal oxide having the empirical formula:

$$Mo_{1.0}V_{0.12-0.49}Te_{0.05-0.25}Nb_{0.10-0.20}Al_{0-2.0}O_d$$

wherein d is a number to satisfy the valence of the oxide. The catalyst composition is at least 40 wt. % amorphous.

The catalyst composition can be prepared by a method that includes providing a mixture including the alumina, a water, and an oxidative dehydrogenation catalyst precursor, removing at least 40 wt. % of the water from the mixture to provide a pre-calcination catalyst composition, and calcining the pre-calcination catalyst composition to provide the catalyst composition. The oxidative dehydrogenation catalyst precursor includes a mixed metal oxide having the empirical formula:

$$Mo_{1.0}V_{0.12-0.49}Te_{0.05-0.17}Nb_{0.10-0.20}Nb_{0.10-0.20}O_d$$

wherein d is a number to satisfy the valence of the oxide.

In some embodiments, the water is selected from distilled water, deionized water, demineralized water, mineral water, or a combination thereof. In some embodiments, the water includes distilled water.

In some embodiments, the water is present in an amount from about 10 wt. % to about 99 wt. % of the mixture. For example, the water can be present in an amount from about 40 wt. % to about 60 wt. % of the mixture.

In some embodiments, the pre-calcination catalyst composition is calcined at a temperature from about 300° C. to about 450° C. For example, the pre-calcination catalyst composition can be calcined at a temperature from about 325° C. to about 375° C. In some embodiments, the pre-calcination catalyst composition is calcined at a temperature of about 350° C.

In some embodiments, the mixture including the oxidative dehydrogenation catalyst precursor, the alumina, and the water is heated at a temperature from about 60° C. to about 100° C. to remove at least 40% of the water. For example, the mixture including the oxidative dehydrogenation catalyst precursor, the alumina, and the water can be heated at a temperature from about 70° C. to about 90° C. to remove at least 40% of the water. In some embodiments, the mixture including the oxidative dehydrogenation catalyst precursor, the alumina, and the water is heated at a temperature of about 80° C. to remove at least 40% of the water.

Also provided herein is a method of preparing a catalyst composition that includes an alumina and an oxidative dehydrogenation catalyst including a mixed metal oxide having the empirical formula:

$$Mo_{1.0}V_{0.12-0.49}Te_{0.05-0.25}Nb_{0.10-0.20}Al_{0-2.0}O_d$$

wherein d is a number to satisfy the valence of the oxide. The method includes providing a mixture that includes the alumina, a water, and an oxidative dehydrogenation catalyst precursor, heating the mixture to remove at least 40 wt. % of the water to provide a pre-calcination catalyst composition, and calcining the pre-calcination catalyst composition to provide the catalyst composition. The oxidative dehydrogenation catalyst precursor includes a mixed metal oxide having the empirical formula:

$$Mo_{1.0}V_{0.12-0.49}Te_{0.05-0.25}Nb_{0.10-0.20}Nb_{0.10-0.20}O_d$$

wherein d is a number to satisfy the valence of the oxide.

In some embodiments, the mixture includes about 20 wt. % to about 90 wt. % of the water, about 5 wt. % to about 50 wt. % of the oxidative dehydrogenation catalyst, and about 5 wt. % to about 30 wt. % of the alumina. In some embodiments, the mixture includes about 40 wt. % to about 60 wt. % of the water, about 25 wt. % to about 35 wt. % of the mixed metal oxide catalyst, and about 15 wt. % to about 25 wt. % of the alumina.

In some embodiments, the mixture is heated at a temperature from about 60° C. to about 100° C. For example, the mixture can be heated at a temperature from about 70° C. to about 90° C. In some embodiments, the mixture is heated at a temperature of about 80° C.

In some embodiments, heating the mixture removes about 40 wt. % to about 99.9 wt. % of the water.

In some embodiments, the calcination temperature is about 300° C. to about 450° C. For example, the calcination temperature can be about 325° C. to about 375° C. In some embodiments, the calcination temperature is about 350° C.

In some embodiments, the calcination time is about 1 hour to about 48 hours. In some embodiments, the calcination time is about 1 hour to about 12 hours. In some embodiments, the calcination time is about 1 hour to about 4 hours. In some embodiments, the calcination time is about 2 hours.

In some embodiments, the calcination temperature is about 300° C. to about 450° C. and the calcination time is about 1 hour to about 48 hours. For example, the calcination temperature can be about 325° C. to about 375° C. and the calcination time is about 1 hour to about 4 hours. In some embodiments, the calcination temperature is about 350° C. to and the calcination time is about 2 hours.

In some embodiments, the amorphous content of the catalyst composition is greater than the predicted additive amorphous content for the catalyst composition.

Also, provided herein is a method of increasing the amorphous phase of a catalyst composition that includes an oxidative dehydrogenation catalyst including a mixed metal oxide having the empirical formula:

$$Mo_{1.0}V_{0.12-0.49}Te_{0.05-0.25}Nb_{0.10-0.20}Al_cO_d$$

wherein c is from 0 to 2.0 and d is a number to satisfy the valence of the oxide. The method includes providing a mixture including the oxidative dehydrogenation catalyst, an alumina, and a water, heating the mixture to remove at least 40 wt. % of the water to provide a pre-calcination catalyst composition, and calcining the pre-calcination catalyst composition to provide the catalyst composition.

Also provided herein is a catalyst composition that includes molybdenum, vanadium, tellurium, niobium, aluminum and oxygen. The molar ratio of molybdenum to vanadium is from 1:0.12 to 1:0.49, as determined by PIXE. The molar ratio of molybdenum to tellurium is from 1:0.05 to 1:0.25, as determined by PIXE. The molar ratio of molybdenum to niobium is from 1:0.10 to 1:0.20, as determined by PIXE. The molar ratio of molybdenum to aluminum is from 0.01 to 2.0, as determined by PIXE. Oxygen is present at least in an amount to satisfy the valency of any present metal oxides. Further, the composition is at least 40 wt. % amorphous as measured by XRD.

In some embodiments, the molar ratio of molybdenum to vanadium is from 1:0.20 to 1:0.45, as determined by PIXE; the molar ratio of molybdenum to tellurium is from 1:0.10 to 1:0.20, as determined by PIXE; the molar ratio of molybdenum to niobium is from 1:0.10 to 1:0.20, as determined by PIXE, and the molar ratio of molybdenum to aluminum is from 0.05 to 0.5, as determined by PIXE.

In some embodiments, the molar ratio of molybdenum to vanadium is from 1:0.30 to 1:0.45, as determined by PIXE; the molar ratio of molybdenum to tellurium is from 1:0.12 to 1:0.18, as determined by PIXE; the molar ratio of molybdenum to niobium is from 1:0.12 to 1:0.18, as determined by PIXE; and the molar ratio of molybdenum to aluminum is from 0.10 to 0.30, as determined by PIXE.

The catalyst composition can be 60 wt. % to 80 wt. % amorphous.

In some embodiments, the source of aluminum in the catalyst composition is derived from a boehmite, such as a pseudoboehmite.

In some embodiments, the catalyst composition is characterized by having XRD diffraction peaks (2θ degrees) at least at 22±0.2, 27±0.2, 28.0±0.2, and 28.3±0.2, wherein the XRD is obtained using CuKα radiation.

In some embodiments, the catalyst composition has a 35% conversion temperature of about 340° C. to about 390° C. For example, the catalyst composition can have a 35% conversion temperature of about 350° C. to about 370° C.

In some embodiments, the catalyst composition has a selectivity to ethylene of greater than about 90%. For example, the catalyst composition can have a selectivity to ethylene of greater than about 93%.

In some embodiments, wherein the catalyst composition has a 35% conversion temperature of about 350° C. to about 390° C. and a selectivity to ethylene of greater than about 90%. For example, the catalyst composition can have a 35% conversion temperature of about 360° C. to about 370° C. and a selectivity to ethylene of greater than about 93%.

The catalyst composition can be prepared by a method that includes providing a mixture comprising the alumina, a water, and an oxidative dehydrogenation catalyst precursor comprising a mixed metal oxide having the empirical formula:

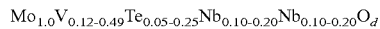

$$Mo_{1.0}V_{0.12-0.49}Te_{0.05-0.25}Nb_{0.10-0.20}Nb_{0.10-0.20}O_d$$

wherein d is a number to satisfy the valence of the oxide; removing at least 40 wt. % of the water from the mixture to provide a pre-calcination catalyst composition; and calcining the pre-calcination catalyst composition to provide the catalyst composition.

In some embodiments, the water is selected from distilled water, deionized water, demineralized water, mineral water, or a combination thereof. For example, the water can include a distilled water. The water can be present in an amount of about 10 wt. % to about 99 wt. % of the mixture. For example, the water can be present in an amount of about 40 wt. % to about 60 wt. % of the mixture.

In some embodiments, the pre-calcination catalyst composition is calcined at a temperature of about 300° C. to about 450° C. For example, the pre-calcination catalyst composition can be calcined at a temperature of about 325° C. to about 375° C. In some embodiments, the pre-calcination catalyst composition is calcined at a temperature of about 350° C.

In some embodiments, the mixture that includes the oxidative dehydrogenation catalyst precursor, the alumina, and the water is heated at a temperature of about 60° C. to about 100° C. to remove at least 40% of the water. For example, the mixture that includes the oxidative dehydrogenation catalyst precursor, the alumina, and the water can be heated at a temperature of about 70° C. to about 90° C. to remove at least 40% of the water.

In some embodiments, the mixture that includes the oxidative dehydrogenation catalyst precursor, the alumina, and the water is heated at a temperature of about 80° C. to remove at least 40% of the water.

Also provided herein is a method for the oxidative dehydrogenation of ethane to ethylene in an oxidative dehydrogenation reactor with a catalyst composition provided in this disclosure.

DETAILED DESCRIPTION

Figure 1A:
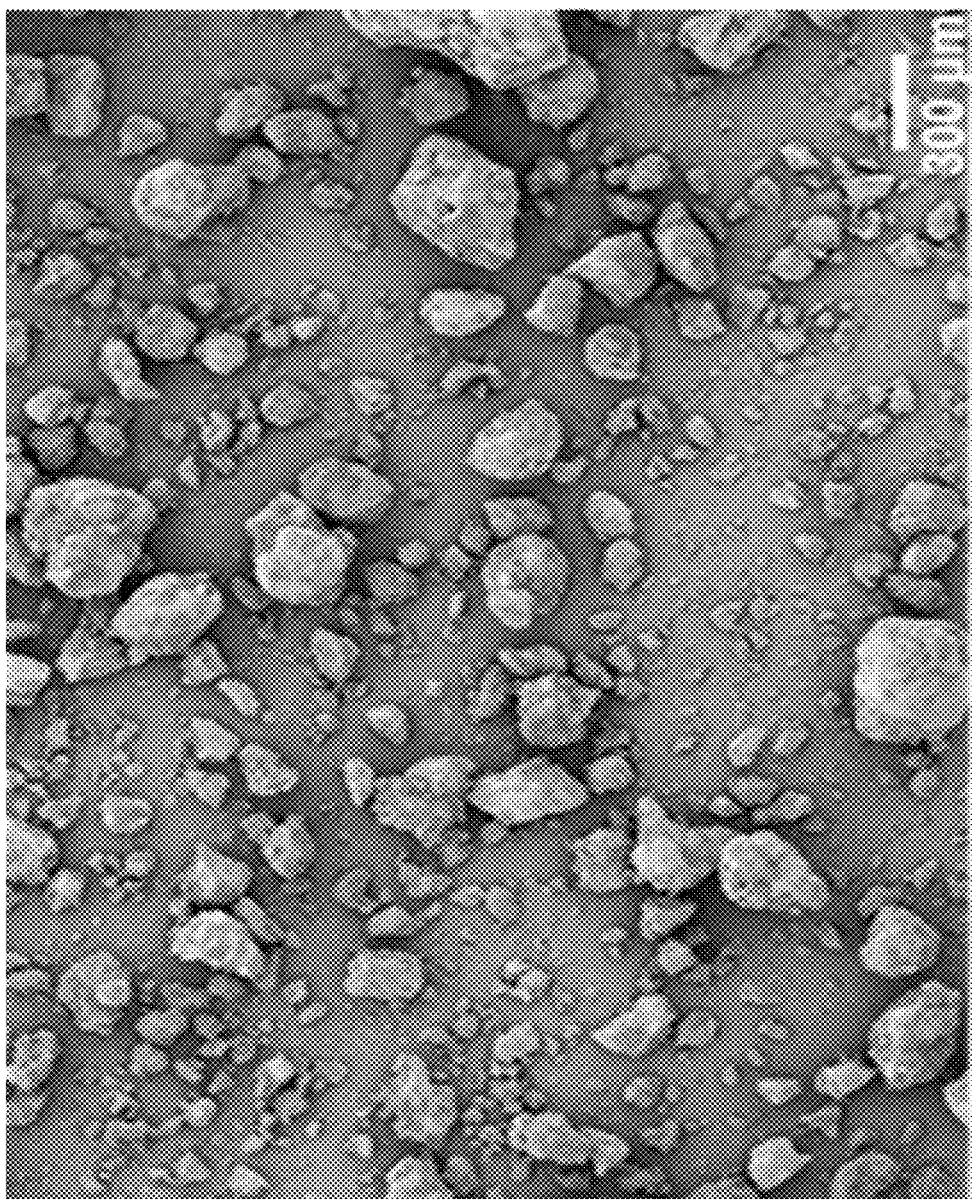
FIG. 1A shows an SEM image of CATAPAL® B alumina binder and an oxidative dehydrogenation catalyst (Catalyst Composition 3.1).

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. A comma can be used as a delimiter or digit group separator to the left or right of a decimal mark; for example, "0.000,1" is equivalent to "0.0001." All publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "room temperature" as used herein refers to a temperature from about 15° C. to about 28° C.

Provided in this disclosure is a catalyst composition including an oxidative dehydrogenation catalyst that includes a mixed metal oxide having the empirical formula:

$$Mo_{1.0}V_{0.12-0.49}Te_{0.05-0.25}Nb_{0.10-0.20}Al_cO_d$$

wherein c is from 0 to 2.0 and d is a number to satisfy the valence of the oxide. The catalyst composition is at least 40 wt. % amorphous. Unless stated otherwise, the amorphous content of the oxidative dehydrogenation catalyst can be determined by X-ray diffraction (XRD).

The empirical formula of the mixed metal oxide can be determined, for example, by inductively coupled plasma mass spectrometry (ICP-MS), particle-induced X-ray emission (PIXE), or both.

In some embodiments, c is 0.01 to 2.0. For example, c can be 0.5 to 1.5.

In some embodiments, the mixed metal oxide has the empirical formula:

$$Mo_{1.0}V_{0.12-0.49}Te_{0.05-0.17}Nb_{0.10-0.20}Al_{0-2.0}O_d$$

wherein d is a number to satisfy the valence of the oxide.

In some embodiments, the mixed metal oxide has the empirical formula:

$$Mo_{1.0}V_{0.12-0.49}Te_{0.05-0.17}Nb_{0.10-0.20}Al_{0.60-1.0}O_d$$

wherein d is a number to satisfy the valence of the oxide.

In some embodiments, the mixed metal oxide has the empirical formula:

$$Mo_{1.0}V_{0.12-0.49}Te_{0.05-0.17}Nb_{0.10-0.20}O_d$$

wherein d is a number to satisfy the valence of the oxide.

The composition can be about 40 wt. % to about 90 wt. % amorphous, about 55 wt. % to about 80 wt. % amorphous, or about 60 wt. % to about 80 wt. % amorphous. For example, the composition can be about 70 wt. % to about 80 wt. % amorphous. In some embodiments, the composition is about 70 wt. %, 75 wt. %, or about 80 wt. % amorphous.

The composition can further include an adjuvant. As used herein, the term "adjuvant" includes materials or compounds that are capable of functioning as a support, a binder, an agglomerating agent, a promoter, an agent capable of at least partially reacting with the oxidative dehydrogenation catalyst, or a combination thereof. In some embodiments, the adjuvant includes an alumina.

The adjuvant can be present in an amount from about 30 weight percent (wt. %) to about 90 wt. %, about 40 wt. % to about 80 wt. %, or about 50 wt. % to about 70 wt. % of the catalyst composition. In some embodiments, the adjuvant is present in an amount from about 50 wt. % to about 65 wt. % of the catalyst composition, such as about 55 wt. % or about 60 wt. % of the catalyst composition. In some embodiments, the adjuvant is present in an amount from about 60 wt. % to about 75 wt. % of the catalyst composition, such as about 70 wt. % of the catalyst composition.

The oxidative dehydrogenation catalyst can be present in an amount from about 10 wt. % to about 70 wt. %, about 20 wt. % to about 60 wt. %, or about 30 wt. % to about 50 wt. % of the catalyst composition. In some embodiments, the oxidative dehydrogenation catalyst is present in an amount from about 35 wt. % to about 45 wt. % of the catalyst composition. For example, the oxidative dehydrogenation catalyst can be present in an amount of about 40 wt. % of the catalyst composition. In some embodiments, the oxidative dehydrogenation catalyst is present in an amount from about 25 wt. % to about 35 wt. % of the catalyst composition. For example, the oxidative dehydrogenation catalyst can be present in an amount of about 30 wt. % of the catalyst composition.

In some embodiments, the adjuvant includes an alumina. The alumina can be selected from an aluminum oxide, an alumina monohydrate, an alumina trihydrate, an alumina-silica, a bauxite, a calcined alumina, a transition alumina, a calcined hydrotalcite, or a combination thereof. The calcined alumina can include a gibbsite, a bayerite, a boehmite, or a combination thereof. In some embodiments, the alumina is a boehmite. As used herein, the term "boehmite" includes, but is not limited to, pseudoboehmites. In some embodiments, the adjuvant is a pseudoboehmite. For example, the adjuvant can be the pseudoboehmite VERSAL™ 250. VERSAL™ 250 has a dispersibility index (%<1mu) of 20-30, a bulk density of 12-16 pounds per cubic foot (lbs/ft³), a surface area of about 320 meters squared per gram (m²/g), and a loss on ignition (LOI) of about 26 wt. %. The dispersibility index for VERSAL™ 250 can be determined by using 8 grams of sample on a volatile free basis and 96 milliliters (mL) of 0.22 normal (N) nitric acid solution, which is approximately 260 meq nitric acid per 100 grams (g) of alumina, mixing the acidic alumina slurry in a WARING® blender at low speed (17000 rpm) for 5 min, and then determining particle size distribution by using a SEDIGRAPH® PSA—with the results reported as wt. % submicron particles. The adjuvant can also be the boehmite CATAPAL® B. CATAPAL® B is an alumina hydrate that has a loose bulk density of 670 to 750 g/L, a packed bulk density of 800 to 1100 g/L, a particle size ($d_{50}$) of 60 μm, a surface area (BET) after activation at 550° C. for 3 hours of 250 m²/g, a pore volume after activation at 550° C. for 3 hours of 0.5 ml/g, and a crystallite size (120) of about 4.5 nm.

In some embodiments, the alumina, such as a boehmite, is present an amount of about 30 wt. % to about 90 wt. %, of the catalyst composition and the oxidative dehydrogenation catalyst is present in an amount of about 10 wt. % to about 70 wt. % of the catalyst composition. For example, the alumina, such as a boehmite, can be present an amount of about 50 wt. % to about 70 wt. %, of the catalyst composition and the oxidative dehydrogenation catalyst can be present in an amount of about 30 wt. % to about 50 wt. % of the catalyst composition. In some embodiments, the alumina, such as a boehmite, is present an amount of about 50 wt. % to about 65 wt. % of the catalyst composition and the oxidative dehydrogenation catalyst is present in an amount of about 35 wt. % to about 45 wt. % of the catalyst composition. For example, the alumina, such as a boehmite, can present an amount of about 55 wt. % or about 60 wt. % of the catalyst composition and the oxidative dehydrogenation catalyst can be present in an amount of about 40 wt. % of the catalyst composition.

In some embodiments, when the composition includes an alumina as an adjuvant, the molar ratio of molybdenum to vanadium in the catalyst composition is from 1:0.12 to 1:0.49, the molar ratio of molybdenum to tellurium in the catalyst composition is from 1:0.05 to 1:0.25, the molar ratio of molybdenum to niobium in the catalyst composition is from 1:0.10 to 1:0.20, and the molar ratio of molybdenum to aluminum in the catalyst composition is from 0.01 to 2.0, as determined by PIXE. In some embodiments, when the composition includes an alumina as an adjuvant, the molar ratio of molybdenum to vanadium in the catalyst composition is from 1:0.20 to 1:0.45, the molar ratio of molybdenum to tellurium in the catalyst composition is from 1:0.10 to 1:0.20, the molar ratio of molybdenum to niobium in the catalyst composition is from 1:0.10 to 1:0.20, and the molar ratio of molybdenum to aluminum in the catalyst composition is from 0.05 to 0.5, as determined by PIXE. In some embodiments, when the composition includes an alumina as an adjuvant, the molar ratio of molybdenum to vanadium in the catalyst composition is from 1:0.30 to 1:0.45, the molar ratio of molybdenum to tellurium in the catalyst composition is from 1:0.12 to 1:0.18, the molar ratio of molybdenum to niobium in the catalyst composition is from 1:0.12 to 1:0.18, and the molar ratio of molybdenum to aluminum in the catalyst composition is from 0.10 to 0.30, as determined by PIXE.

The catalyst composition can be characterized by having XRD diffraction peaks (2θ degrees) at least at 22±0.2, 27±0.2, 28.0±0.2, and 28.3±0.2, wherein the XRD is obtained using CuKα radiation.

It should also be understood that the catalyst compositions disclosed herein are not limited to those that provide XRD patterns that are identical to the XRD patterns shown in the Figures, and that any catalyst compositions providing XRD patterns substantially the same as those shown in the Figures fall within the scope of the corresponding embodiment. A person skilled in the art of XRD is able to judge the substantial identity of XRD patterns. Generally, a measurement error of a diffraction angle in an XRD is approximately 2θ(±0.2° or ±0.10), and such degree of a measurement error should be taken into account when considering the X-ray diffraction pattern in the Figures and when reading data contained in the Tables included herein.

In some embodiments, the catalyst composition has a 35% conversion temperature of about 340° C. to about 390° C. For example, the catalyst composition can have a 35% conversion temperature of about 350° C. to about 370° C. In some embodiments, the catalyst composition has a 35% conversion temperature of about 350° C., 355° C., 360° C., 365° C., or about 370° C.

As used in this disclosure, the phrase "35% conversion temperature" refers to the temperature at which 35% of ethane in a gas stream is converted to a product other than ethane. The 35% conversion temperature of an oxidative dehydrogenation catalyst can be determined by using a microreactor unit (MRU). In a microreactor unit, the 35% conversion temperature of a catalyst can be determined by passing a feed gas over a catalyst bed in a reactor tube. The MRU reactor tube has an outer diameter of about 0.5 inches and an internal diameter of about 0.4 inches and length of about 15 inches. For example, the reactor tube can be stainless-steel SWAGELOK® Tubing with a wall thickness of about 0.049 inches. The feed gas can include ethane and oxygen having a molar ratio of 70:30 to 90:10. For example, the feed gas can include ethane and oxygen having a molar ratio of 82:18. Alternatively, the feed gas can include ethane, oxygen, and nitrogen. The molar ratio of ethane to oxygen to nitrogen can be 18:18:64 to 54:18:28. For example, the molar ratio of ethane to oxygen to nitrogen can be 36:18:46 or 35:17.5:47.5. The flow rate of the feed gas can be about 70 standard cubic centimeters per minute (sccm) to about 80 sccm. For example, the flow rate of the feed gas can be about 75 sccm (e.g., 74.6 sccm). The catalyst bed consists of the oxidative dehydrogenation catalyst and a filler, such as sand, in a one to one volume ratio, with the total weight for the oxidative dehydrogenation catalyst being 1.96 g. Any remaining space in the reactor tube (e.g., below or above the catalyst bed) is packed with an additional filler, such as quartz sand. The 35% conversion temperature is determined at a weight hourly space velocity (WHSV) of 2.90 h$^{-1}$, with the WHSV based on the active phase, and a gas hourly space velocity (GHSV) of about 2,000 to 3,000 h$^{-1}$. Typically, the inlet pressure is in the range of about 1 pound per square inch gauge (psig) to about 2.5 psig and the outlet pressure is in the range of about 0 psig to about 0.5 psig. The gas feed exiting the catalyst bed is analyzed by gas chromatography to determine the percent of various hydrocarbons (e.g., ethane and ethylene) and, optionally other gases such as $O_2$, $CO_2$, and CO. Conversion of the feed gas is calculated as a mass flow rate change of ethane in the product compared to feed ethane mass flow rate using the following formula:

$$C = \left( \frac{2 * X_{Ethylene} + X_{CO2} + X_{CO}}{2 * X_{Ethylene} + X_{Ethane} + X_{CO2} + X_{CO}} \right) * 100\%$$

wherein C is the percent of feed gas that has been converted from ethane to another product (i.e., ethane conversion) and X is the molar concentration of the corresponding compound in the gaseous effluent exiting the reactor. The ethane conversion is then plotted as a function of temperatures to acquire a linear algebraic equation. The linear equation for ethane conversion is solved to determine the temperature in which the ethane conversion is 35% (i.e. the 35% conversion temperature). Not taken into account for calculating the 35% conversion temperature or selectivity to ethane, described below, were reaction products exiting the reactor in an aqueous stream such as, but not limited to, acetic acid, maleic acid, propionic acid, ethanol, and acetaldehyde.

In some embodiments, the catalyst composition has a 35% conversion temperature of about 340° C. to about 390° C. under MRU testing as described herein with a feed gas of ethane, oxygen, and nitrogen at molar ratio of 35:17.5:47.5, a flow rate of about 75 sccm, and a WHSV of 2.90 h$^{-1}$. For example, the catalyst composition can have a 35% conversion temperature of about 350° C. to about 370° C. under MRU testing as described herein with a feed gas of ethane, oxygen, and nitrogen at molar ratio of 35:17.5:47.5 and a flow rate of about 75 sccm. In some embodiments, the catalyst composition has a 35% conversion temperature of about 350° C., 355° C., 360° C., 365° C., or about 370° C. under MRU testing as described herein with a feed gas of ethane, oxygen, and nitrogen at molar ratio of 35:17.5:47.5 and a flow rate of about 75 sccm.

The catalyst composition can have a selectivity to ethylene of greater than about 85%. For example, the catalyst composition can have a selectivity to ethylene of about 85% to about 99%, about 90% to about 99%, about 92% to about 99%, or about 93% to about 98%.

As used in this disclosure, the phrase "selectivity to ethylene" refers to the percentage on a molar basis of converted or reacted ethane that forms ethylene. An oxidative dehydrogenation catalyst's selectivity to ethylene can be determined using an MRU as discussed above. An oxidative dehydrogenation catalyst's selectivity to ethylene can be determined using to the following equation:

$$S_{Ethylene} = \left( \frac{2 * X_{Ethylene}}{2 * X_{EWthylene} + X_{CO2} + X_{CO}} \right) * 100\%$$

wherein $S_{Ethylene}$ is the selectivity to ethylene, and X is the molar concentration of the corresponding compound in the gaseous effluent exiting the reactor. Notably, the selectivity to ethylene is determined at the 35% conversion temperature, unless otherwise indicated. As such, after the 35% conversion temperature is determined, the above equation for selectivity is solved using the corresponding values for $X_{Ethylene}$, $X_{CO2}$, and $X_{CO}$ at the 35% conversion temperature.

In some embodiments, the catalyst composition has a selectivity to ethylene of greater than about 85% under MRU testing as described herein with a feed gas of ethane, oxygen, and nitrogen at molar ratio of 35:17.5:47.5 and a flow rate of about 75 sccm. For example, the catalyst composition can have a selectivity to ethylene of about 85% to about 99%, about 90% to about 99%, about 92% to about 99%, or about 93% to about 98% under MRU testing as described herein with a feed gas of ethane, oxygen, and nitrogen at molar ratio of 35:17.5:47.5 and a flow rate of about 75 sccm.

In some embodiments, the catalyst composition has a 35% conversion temperature of about 350° C. to about 390° C. and a selectivity to ethylene of greater than about 85%. For example, the catalyst composition can have a 35% conversion temperature of about 350° C. to about 370° C. and a selectivity to ethylene of about 93% to about 98%.

In some embodiments, the catalyst composition has a 35% conversion temperature of about 350° C. to about 390° C. and a selectivity to ethylene of greater than about 90% under MRU testing as described herein with a feed gas of ethane, oxygen, and nitrogen at molar ratio of 35:17.5:47.5 and a flow rate of about 75 sccm. In some embodiments, the catalyst composition has a 35% conversion temperature of about 350° C. to about 370° C. and a selectivity to ethylene of greater than about 90% under MRU testing as described herein with a feed gas of ethane, oxygen, and nitrogen at molar ratio of 35:17.5:47.5 and a flow rate of about 75 sccm. For example, the catalyst composition can have a 35% conversion temperature of about 350° C. to about 370° C. and a selectivity to ethylene of about 93% to about 98% under MRU testing as described herein with a feed gas of ethane, oxygen, and nitrogen at molar ratio of 35:17.5:47.5 and a flow rate of about 75 sccm.

Also provided in this disclosure is a catalyst composition that includes a boehmite and an oxidative dehydrogenation catalyst. The oxidative dehydrogenation catalyst includes a mixed metal oxide having the empirical formula:

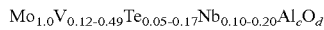
$$Mo_{1.0}V_{0.12-0.49}Te_{0.05-0.17}Nb_{0.10-0.20}Al_cO_d$$

wherein c is 0 to 2.0 and d is a number to satisfy the valence of the oxide. The boehmite is present in an amount of about 50 wt. % to about 70 wt. % of the catalyst composition. The oxidative dehydrogenation catalyst is present in an amount of about 30 wt. % to about 50 wt. % of the catalyst composition. The catalyst composition is about 60 wt. % to about 80 wt. % amorphous as measured by XRD.

In some embodiments, the molar ratio of molybdenum to vanadium in the catalyst composition is from 1:0.20 to 1:0.45, the molar ratio of molybdenum to tellurium in the catalyst composition is from 1:0.10 to 1:0.20, the molar ratio of molybdenum to niobium in the catalyst composition is from 1:0.10 to 1:0.20, and the molar ratio of molybdenum to aluminum in the catalyst composition is from 0.05 to 0.5, as determined by PIXE. In some embodiments, when the composition includes an alumina as an adjuvant, the molar ratio of molybdenum to vanadium in the catalyst composition is from 1:0.30 to 1:0.45, the molar ratio of molybdenum to tellurium in the catalyst composition is from 1:0.12 to 1:0.18, the molar ratio of molybdenum to niobium in the catalyst composition is from 1:0.12 to 1:0.18, and the molar ratio of molybdenum to aluminum in the catalyst composition is from 0.10 to 0.30, as determined by PIXE.

In some embodiments, c is 0.01 to 2.0 or 0.5 to 1.5. For example, the mixed metal oxide can have the empirical formula:

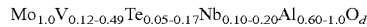
$$Mo_{1.0}V_{0.12-0.49}Te_{0.05-0.17}Nb_{0.10-0.20}Al_{0.60-1.0}O_d$$

wherein d is a number to satisfy the valence of the oxide.

In some embodiments, the catalyst composition has a 35% conversion temperature of about 350° C. to about 370° C. and a selectivity to ethylene of greater than about 90%. For example, the catalyst composition can have a 35% conversion temperature of about 350° C. to about 370° C. and a selectivity to ethylene of greater than about 90% under MRU testing as described herein with a feed gas of ethane, oxygen, and nitrogen at molar ratio of 35:17.5:47.5 and a flow rate of about 75 sccm. In some embodiments, the catalyst composition has a 35% conversion temperature of about 350° C. to about 370° C. and a selectivity to ethylene of about 93% to about 98% under MRU testing as described herein with a feed gas of ethane, oxygen, and nitrogen at molar ratio of 35:17.5:47.5 and a flow rate of about 75 sccm.

Further provided in this disclosure is a catalyst composition that includes a boehmite and an oxidative dehydrogenation catalyst. The oxidative dehydrogenation catalyst includes a mixed metal oxide having the empirical formula:

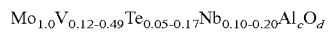
$$Mo_{1.0}V_{0.12-0.49}Te_{0.05-0.17}Nb_{0.10-0.20}Al_cO_d$$

wherein c is 0 to 2.0 and d is a number to satisfy the valence of the oxide. The boehmite is present in an amount of about 50 wt. % to about 70 wt. % of the catalyst composition. The oxidative dehydrogenation catalyst is present in an amount of about 30 wt. % to about 50 wt. % of the catalyst composition. The catalyst composition is about 60 wt. % to about 80 wt. % amorphous as measured by XRD. The catalyst composition has a 35% conversion temperature of about 350° C. to about 370° C. and a selectivity to ethylene of greater than about 90%.

In some embodiments, when the composition includes an alumina as an adjuvant, the molar ratio of molybdenum to vanadium in the catalyst composition is from 1:0.20 to 1:0.45, the molar ratio of molybdenum to tellurium in the catalyst composition is from 1:0.10 to 1:0.20, the molar ratio of molybdenum to niobium in the catalyst composition is from 1:0.10 to 1:0.20, and the molar ratio of molybdenum to aluminum in the catalyst composition is from 0.05 to 0.5, as determined by PIXE. In some embodiments, when the composition includes an alumina as an adjuvant, the molar ratio of molybdenum to vanadium in the catalyst composition is from 1:0.30 to 1:0.45, the molar ratio of molybdenum to tellurium in the catalyst composition is from 1:0.12 to 1:0.18, the molar ratio of molybdenum to niobium in the catalyst composition is from 1:0.12 to 1:0.18, and the molar ratio of molybdenum to aluminum in the catalyst composition is from 0.10 to 0.30, as determined by PIXE.

In some embodiments, c is 0.01 to 2.0 or 0.5 to 1.5. For example, the mixed metal oxide can have the empirical formula:

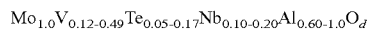
$$Mo_{1.0}V_{0.12-0.49}Te_{0.05-0.17}Nb_{0.10-0.20}Al_{0.60-1.0}O_d$$

wherein d is a number to satisfy the valence of the oxide.

Also provided in this disclosure is a catalyst composition that includes an alumina and an oxidative dehydrogenation catalyst. The oxidative dehydrogenation catalyst includes a mixed metal oxide having the empirical formula:

$$Mo_{1.0}V_{0.12-0.49}Te_{0.05-0.17}Nb_{0.10-0.20}Al_cO_d$$

wherein c is 0 to 2.0 and d is a number to satisfy the valence of the oxide. The catalyst composition is at least 40 wt. % amorphous as measured by XRD. The catalyst composition is prepared by a method that includes providing a mixture including the alumina, a water, and an oxidative dehydrogenation catalyst precursor. The oxidative dehydrogenation catalyst precursor can include a mixed metal oxide having the empirical formula:

$$Mo_{1.0}V_{0.12-0.49}Te_{0.05-0.17}Nb_{0.10-0.20}O_d$$

wherein d is a number to satisfy the valence of the oxide. The method of preparing the catalyst composition further includes removing at least 40 wt. % of the water from the mixture to provide a pre-calcination catalyst composition. The method further includes calcining the pre-calcination catalyst composition to provide the catalyst composition.

During the process of removing at least 40 wt. % of the water from the mixture, calcining the pre-calcination composition, or both, the alumina can at least partially react with the oxidative dehydrogenation catalyst precursor, which can result in the incorporation of alumina, aluminum, or both into the oxidative dehydrogenation catalyst precursor to yield the oxidative dehydrogenation catalyst with a mixed metal oxide having the empirical formula:

$$Mo_{1.0}V_{0.12-0.49}Te_{0.05-0.17}Nb_{0.10-0.20}Al_cO_d$$

wherein c is greater than 0. In some embodiments, c is 0.01 to 2.0. For example, c can be 0.5 to 1.5 or 0.60 to 1.0.

In some embodiments, neither alumina nor aluminum react with the oxidative dehydrogenation catalyst precursor, in which case aluminum and alumina are not incorporated into the mixed metal oxide of the oxidative dehydrogenation catalyst precursor.

In some embodiments, the molar ratio of molybdenum to vanadium in the catalyst composition is from 1:0.20 to 1:0.45, the molar ratio of molybdenum to tellurium in the catalyst composition is from 1:0.10 to 1:0.20, the molar ratio of molybdenum to niobium in the catalyst composition is from 1:0.10 to 1:0.20, and the molar ratio of molybdenum to aluminum in the catalyst composition is from 0.05 to 0.5, as determined by PIXE. In some embodiments, when the composition includes an alumina as an adjuvant, the molar ratio of molybdenum to vanadium in the catalyst composition is from 1:0.30 to 1:0.45, the molar ratio of molybdenum to tellurium in the catalyst composition is from 1:0.12 to 1:0.18, the molar ratio of molybdenum to niobium in the catalyst composition is from 1:0.12 to 1:0.18, and the molar ratio of molybdenum to aluminum in the catalyst composition is from 0.10 to 0.30, as determined by PIXE.

Figure 1B:
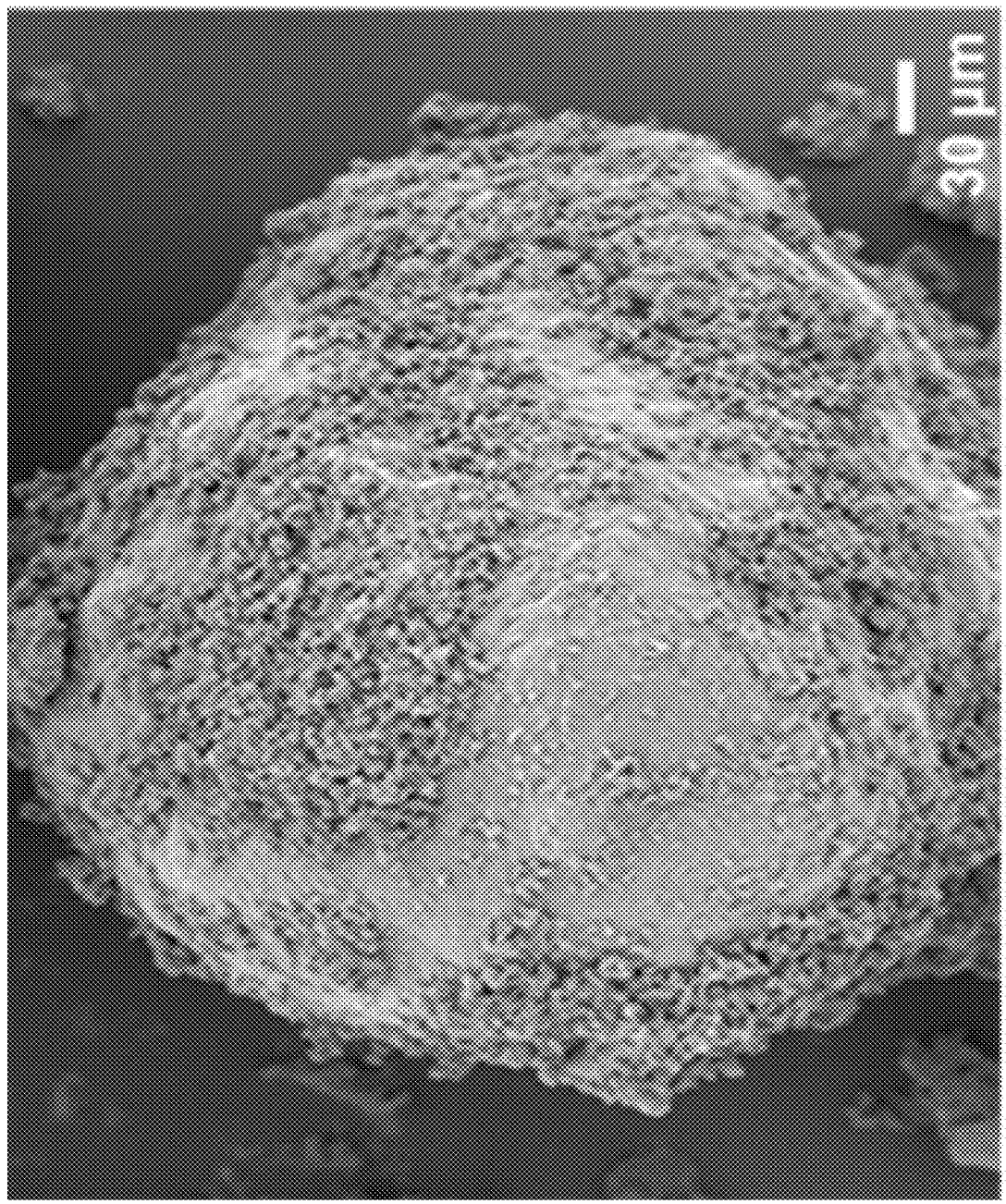
FIG. 1B shows an SEM image of CATAPAL® B alumina binder and an oxidative dehydrogenation catalyst (Catalyst Composition 3.1).

Removing at least 40 wt. % of the water from the mixture, calcining the pre-calcination composition, or both, can also provide a catalyst composition in which the alumina is at least partially coated with the oxidative dehydrogenation catalyst—as shown, for example, in FIGS. 1A and 1B. The alumina core that can be coated with the oxidative dehydrogenation catalyst can have an average particle size of about 0.1 nanometers to about 10 nm, about 2 nm to about 8 nm, or about 3 nm to about 6 nm.

The water in the mixture can be selected from distilled water, deionized water, demineralized water, mineral water, or a combination thereof. In some embodiments, the water includes distilled water. The water can be present an amount of about 10 wt. % to about 99 wt. %, about 20 wt. % to about 80 wt. %, or about 40 wt. % to about 60 wt. % of the mixture. In some embodiments, the water is present in an amount of about 40 wt. %, about 50 wt. %, or about 60 wt. % of the mixture.

In some embodiments, about 50 wt. % to about 99.9 wt. % of the water is removed from the mixture to provide the pre-calcination catalyst composition. For example, about 50 wt. % to about 70 wt. %, about 70 wt. % to about 90 wt. %, or about 90 wt. % to about 99.9 wt. % of the water can be removed from the mixture to provide the pre-calcination catalyst composition. In some embodiments, the oxidative dehydrogenation catalyst and alumina can be stored in the water for a period of time prior to removing the desired amount of water. For example, the oxidative dehydrogenation catalyst and alumina can be stored in the water for about 15 days, 1 month, 6 months, or about 1 year, prior to removing the desired amount of water.

The desired amount of water can be removed from the mixture by allowing the water to evaporate at room temperature, heating the mixture, or both. For example, the mixture can be heated at a temperature of about 30° C. to about 100° C. or about 60° C. to about 100° C. to remove the desired amount of water. In some embodiments, the mixture is heated at a temperature of about 70° C. to about 90° C. For example, the mixture can be heated at a temperature of about 80° C.

In some embodiments, calcining the pre-calcination catalyst composition to provide the catalyst composition includes calcining the pre-calcination catalyst composition at about 300° C. to about 450° C. For example, the pre-calcination catalyst composition can be calcined at about 325° C. to about 375° C. In some embodiments, the pre-calcination catalyst composition is calcined at about 350° C. to provide the catalyst composition.

The pre-calcination catalyst composition can be calcined for a time of about 1 hour to about 48 hours, about 1 hour to about 12 hours, or about 1 hour to about 4 hours. For example, the pre-calcination catalyst composition can be calcined for about 2 hours.

In some embodiments, calcining the pre-calcination catalyst composition to provide the catalyst composition includes calcining the pre-calcination catalyst composition at about 300° C. to about 450° C. for about 1 hour to about 48 hours. For example, the pre-calcination catalyst composition can be calcined at about 325° C. to about 375° C. for about 1 hour to about 4 hours to provide the catalyst composition. In some embodiments, the pre-calcination catalyst composition is calcined at about 350° C. for 2 hours to provide the catalyst composition.

Also provided in this disclosure is a catalyst composition that includes a boehmite—such as VERSAL™ 250 or CATAPAL® B—and an oxidative dehydrogenation catalyst. The oxidative dehydrogenation catalyst includes a mixed metal oxide having the empirical formula:

$$Mo_{1.0}V_{0.12-0.49}Te_{0.05-0.17}Nb_{0.10-0.20}Al_cO_d$$

wherein c is 0 to 2.0 and d is a number to satisfy the valence of the oxide. The catalyst composition is about 60 wt. % to about 80 wt. % amorphous as measured by XRD. The catalyst composition is prepared by a method that includes providing a mixture including the boehmite, a water, and an oxidative dehydrogenation catalyst precursor. The oxidative dehydrogenation catalyst precursor can include a mixed metal oxide having the empirical formula:

$$Mo_{1.0}V_{0.12-0.49}Te_{0.05-0.17}Nb_{0.10-0.20}O_d$$

wherein d is a number to satisfy the valence of the oxide. The method of preparing the catalyst composition further includes removing at least 40 wt. % of the water from the mixture by heating the mixture at a temperature of about 70° C. to about 90° C. (e.g., 80° C.) to provide a pre-calcination catalyst composition. The method also includes calcining the pre-calcination catalyst at about 325° C. to about 375° C. for about 1 hour to about 4 hours to provide the catalyst composition.

In some embodiments, the molar ratio of molybdenum to vanadium in the catalyst composition is from 1:0.20 to 1:0.45, the molar ratio of molybdenum to tellurium in the catalyst composition is from 1:0.10 to 1:0.20, the molar ratio of molybdenum to niobium in the catalyst composition is from 1:0.10 to 1:0.20, and the molar ratio of molybdenum to aluminum in the catalyst composition is from 0.05 to 0.5, as determined by PIXE. In some embodiments, when the composition includes an alumina as an adjuvant, the molar ratio of molybdenum to vanadium in the catalyst composition is from 1:0.30 to 1:0.45, the molar ratio of molybdenum to tellurium in the catalyst composition is from 1:0.12 to 1:0.18, the molar ratio of molybdenum to niobium in the catalyst composition is from 1:0.12 to 1:0.18, and the molar ratio of molybdenum to aluminum in the catalyst composition is from 0.10 to 0.30, as determined by PIXE.

In some embodiments, c is 0.01 to 2.0 or 0.5 to 1.5. For example, the mixed metal oxide can have the empirical formula:

$$Mo_{1.0}V_{0.12-0.49}Te_{0.05-0.17}Nb_{0.10-0.20}Al_{0.60-1.0}O_d$$

wherein d is a number to satisfy the valence of the oxide.

In some embodiments, the catalyst composition has a 35% conversion temperature of about 350° C. to about 370° C. and a selectivity to ethylene of greater than about 90%. For example, the catalyst composition can have a 35% conversion temperature of about 350° C. to about 370° C. and a selectivity to ethylene of greater than about 90% under MRU testing as described herein with a feed gas of ethane, oxygen, and nitrogen at molar ratio of 35:17.5:47.5 and a flow rate of about 75 sccm. In some embodiments, the catalyst composition has a 35% conversion temperature of about 350° C. to about 370° C. and a selectivity to ethylene of about 93% to about 98% under MRU testing as described herein with a feed gas of ethane, oxygen, and nitrogen at molar ratio of 35:17.5:47.5 and a flow rate of about 75 sccm.

Also provided herein is a method of preparing a catalyst composition that includes an alumina and an oxidative dehydrogenation catalyst. The oxidative dehydrogenation catalyst includes a mixed metal oxide having the empirical formula:

$$Mo_{1.0}V_{0.12-0.49}Te_{0.05-0.17}Nb_{0.10-0.20}Al_cO_d$$

wherein c is 0 to 2.0 and d is a number to satisfy the valence of the oxide. The method includes providing a mixture including the alumina, a water, and an oxidative dehydrogenation catalyst precursor. The oxidative dehydrogenation catalyst precursor includes a mixed metal oxide having the empirical formula:

$$Mo_{1.0}V_{0.12-0.49}Te_{0.05-0.17}Nb_{0.10-0.20}O_d$$

wherein d is a number to satisfy the valence of the oxide. The catalyst composition is at least 40 wt. % amorphous. The method further includes heating the mixture including the oxidative dehydrogenation catalyst precursor, the alumina, and the water to remove at least 50 wt. % of the water to provide a pre-calcination catalyst composition. Additionally, the method includes calcining the pre-calcination catalyst composition to provide the catalyst composition.

The oxidative dehydrogenation catalyst precursor can be prepared as described in U.S. Publication No. 20170050178A1, the disclosure of which is incorporated herein by reference in its entirety.

As discussed herein, during the process of removing at least 40 wt. % of the water from the mixture, calcining the pre-calcination composition, or both, the alumina can at least partially react with the oxidative dehydrogenation catalyst precursor, which can result in incorporation of alumina, aluminum, or both into the mixed metal oxide of the oxidative dehydrogenation catalyst. In such instances, c can be from 0.01 to 2.0 or 0.5 to 1.5. For example, in such instances, the mixed metal oxide can have the empirical formula:

$$Mo_{1.0}V_{0.12-0.49}Te_{0.05-0.17}Nb_{0.10-0.20}Al_{0.60-1.0}O_d$$

wherein d is a number to satisfy the valence of the oxide.

Alternatively, in some embodiments, alumina nor aluminum react with the oxidative dehydrogenation catalyst precursor, in which case alumina nor aluminum are not incorporated into the mixed metal oxide of the oxidative dehydrogenation catalyst precursor. In such instances, the mixed metal oxide of the oxidative dehydrogenation catalyst can have the empirical formula:

$$Mo_{1.0}V_{0.12-0.49}Te_{0.05-0.17}Nb_{0.1-0.20}O_d$$

wherein d is a number to satisfy the valence of the oxide.

In some embodiments, the molar ratio of molybdenum to vanadium in the catalyst composition is from 1:0.20 to 1:0.45, the molar ratio of molybdenum to tellurium in the catalyst composition is from 1:0.10 to 1:0.20, the molar ratio of molybdenum to niobium in the catalyst composition is from 1:0.10 to 1:0.20, and the molar ratio of molybdenum to aluminum in the catalyst composition is from 0.05 to 0.5, as determined by PIXE. In some embodiments, when the composition includes an alumina as an adjuvant, the molar ratio of molybdenum to vanadium in the catalyst composition is from 1:0.30 to 1:0.45, the molar ratio of molybdenum to tellurium in the catalyst composition is from 1:0.12 to 1:0.18, the molar ratio of molybdenum to niobium in the catalyst composition is from 1:0.12 to 1:0.18, and the molar ratio of molybdenum to aluminum in the catalyst composition is from 0.10 to 0.30, as determined by PIXE.

In the mixture, the water can be present in an amount of about 20 wt. % to about 90 wt. % of the mixture, the oxidative dehydrogenation catalyst precursor can be present in an amount of about 5 wt. % to about 50 wt. % of the mixture, and the alumina can be present in an amount of about 5 wt. % to about 30 wt. % of the mixture. In some embodiments, the water the water is present in an amount of about 40 wt. % to about 60 wt. % of the mixture, the oxidative dehydrogenation catalyst precursor is present in an amount of about 25 wt. % to about 35 wt. % of the mixture, and the alumina is present in an amount of about 15 wt. % to about 25 wt. % of the mixture.

In some embodiments, the method further includes agitating the mixture including the oxidative dehydrogenation catalyst precursor, the alumina, and the water before removing at least 40 wt. % of the water, while removing at least 40% of the water, or both.

In some embodiments, about 40 wt. % to about 99.9 wt. % of the water is removed from the mixture to provide the pre-calcination catalyst composition. For example, about 40 wt. % to about 70 wt. %, about 70 wt. % to about 90 wt. %, or about 90 wt. % to about 99.9 wt. % of the water can be removed from the mixture to provide the pre-calcination catalyst composition. In some embodiments, the oxidative dehydrogenation catalyst precursor and alumina can be stored in the water for a period of time prior to removing the desired amount of water. For example, the oxidative dehydrogenation catalyst precursor and alumina can be stored in the water for about 15 days, 1 month, 6 months, or about 1 year, prior to removing the desired amount of water.

The desired amount of water can be removed from the mixture by allowing the water to evaporate at room temperature, heating the mixture, or both. For example, the mixture can be heated at a temperature of about 30° C. to about 100° C. or about 60° C. to about 100° C. to remove the desired amount of water. In some embodiments, the mixture is heated at a temperature of about 70° C. to about 90° C. For example, the mixture can be heated at a temperature of about 80° C.

In some embodiments, calcining the pre-calcination catalyst composition to provide the catalyst composition includes calcining the pre-calcination catalyst composition at about 300° C. to about 450° C. For example, the pre-calcination catalyst composition can be calcined at about 325° C. to about 375° C. In some embodiments, the pre-calcination catalyst composition is calcined at about 350° C. to provide the catalyst composition.

The pre-calcination catalyst composition can be calcined for a time of about 1 hour to about 48 hours, about 1 hour to about 12 hours, or about 1 hour to about 4 hours. For example, the pre-calcination catalyst composition can be calcined for about 2 hours.

In some embodiments, calcining the pre-calcination catalyst composition to provide the catalyst composition includes calcining the pre-calcination catalyst composition at about 300° C. to about 450° C. for about 1 hour to about 48 hours. For example, the pre-calcination catalyst composition can be calcined at about 325° C. to about 375° C. for about 1 hour to about 4 hours to provide the catalyst composition. In some embodiments, the pre-calcination catalyst composition is calcined at about 350° C. for 2 hours to provide the catalyst composition.

In some embodiments, the amorphous content of the catalyst composition is greater than the predicted additive amorphous content for the catalyst composition. For instance, as shown in Example 3.8, a catalyst composition prepared from 60 wt. % of boehmite (a 51.2% amorphous starting material) and 40 wt. % of an oxidative dehydrogenation catalyst (a 42.5% amorphous starting material) has a predicted additive amorphous content of 47.72 wt. % (0.6× 51.2+0.4×42.5=47.72)—however, when prepared as disclosed herein, the catalyst composition can surprisingly have more than the predicted additive amorphous content (see e.g., Catalyst Composition 3.3). In some embodiments, the amorphous content of the catalyst composition is about 5 wt. % to about 50 wt. %, about 10 wt. % to about 45 wt. %, about 20 wt. % to about 40 wt. %, or about 25 wt. % to about 35 wt. % greater than the predicted additive amorphous content for the catalyst composition.

Also provided herein is a catalyst composition that includes molybdenum, vanadium, tellurium, niobium, aluminum and oxygen. The molar ratio of molybdenum to vanadium is from 1:0.12 to 1:0.49, as determined by PIXE. The molar ratio of molybdenum to tellurium is from 1:0.05 to 1:0.25, as determined by PIXE. The molar ratio of molybdenum to niobium is from 1:0.10 to 1:0.20, as determined by PIXE. The molar ratio of molybdenum to aluminum is from 0.01 to 2.0, as determined by PIXE. Oxygen is present at least in an amount to satisfy the valency of any present metal oxides. Further, the composition is at least 40 wt. % amorphous as measured by XRD.

In some embodiments, the molar ratio of molybdenum to vanadium is from 1:0.20 to 1:0.45, as determined by PIXE; the molar ratio of molybdenum to tellurium is from 1:0.10 to 1:0.20, as determined by PIXE; the molar ratio of molybdenum to niobium is from 1:0.10 to 1:0.20, as determined by PIXE, and the molar ratio of molybdenum to aluminum is from 0.05 to 0.5, as determined by PIXE.

In some embodiments, the molar ratio of molybdenum to vanadium is from 1:0.30 to 1:0.45, as determined by PIXE; the molar ratio of molybdenum to tellurium is from 1:0.12 to 1:0.18, as determined by PIXE; the molar ratio of molybdenum to niobium is from 1:0.12 to 1:0.18, as determined by PIXE; and the molar ratio of molybdenum to aluminum is from 0.10 to 0.30, as determined by PIXE.

The catalyst composition can be 60 wt. % to 80 wt. % amorphous.

In some embodiments, the source of aluminum in the catalyst composition is derived from a boehmite, such as a pseudoboehmite.

In some embodiments, the catalyst composition is characterized by having XRD diffraction peaks (2θ degrees) at least at 22±0.2, 27±0.2, 28.0±0.2, and 28.3±0.2, wherein the XRD is obtained using CuKα radiation.

In some embodiments, the catalyst composition has a 35% conversion temperature of about 340° C. to about 390° C. For example, the catalyst composition can have a 35% conversion temperature of about 350° C. to about 370° C.

In some embodiments, the catalyst composition has a selectivity to ethylene of greater than about 90%. For example, the catalyst composition can have a selectivity to ethylene of greater than about 93%.

In some embodiments, wherein the catalyst composition has a 35% conversion temperature of about 350° C. to about 390° C. and a selectivity to ethylene of greater than about 90%. For example, the catalyst composition can have a 35% conversion temperature of about 360° C. to about 370° C. and a selectivity to ethylene of greater than about 93%.

The catalyst composition can be prepared by a method that includes providing a mixture comprising the alumina, a water, and an oxidative dehydrogenation catalyst precursor comprising a mixed metal oxide having the empirical formula:

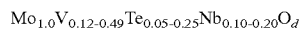

$$Mo_{1.0}V_{0.12-0.49}Te_{0.05-0.25}Nb_{0.10-0.20}O_d$$

wherein d is a number to satisfy the valence of the oxide; removing at least 40 wt. % of the water from the mixture to provide a pre-calcination catalyst composition; and calcining the pre-calcination catalyst composition to provide the catalyst composition.

In some embodiments, the water is selected from distilled water, deionized water, demineralized water, mineral water, or a combination thereof. For example, the water can include a distilled water. The water can be present in an amount of about 10 wt. % to about 99 wt. % of the mixture. For example, the water can be present in an amount of about 40 wt. % to about 60 wt. % of the mixture.

In some embodiments, the pre-calcination catalyst composition is calcined at a temperature of about 300° C. to about 450° C. For example, the pre-calcination catalyst composition can be calcined at a temperature of about 325° C. to about 375° C. In some embodiments, the pre-calcination catalyst composition is calcined at a temperature of about 350° C.

In some embodiments, the mixture that includes the oxidative dehydrogenation catalyst precursor, the alumina, and the water is heated at a temperature of about 60° C. to about 100° C. to remove at least 40% of the water. For example, the mixture that includes the oxidative dehydrogenation catalyst precursor, the alumina, and the water can be heated at a temperature of about 70° C. to about 90° C. to remove at least 40% of the water.

In some embodiments, the mixture that includes the oxidative dehydrogenation catalyst precursor, the alumina, and the water is heated at a temperature of about 80° C. to remove at least 40% of the water.

Also provided herein is a method for the oxidative dehydrogenation of ethane to ethylene in an oxidative dehydrogenation reactor with any catalyst composition described herein.

Also provided herein is a method for the oxidative dehydrogenation of ethane to ethylene in an oxidative dehydrogenation reactor with any oxidative dehydrogenation catalysts or catalyst compositions described herein.

Ethylene can subsequently be converted into a variety of products. For example, ethylene can be converted into many various compounds including low density polyethylene, high density polyethylene, ethylene dichloride, ethylene oxide, ethylbenzene, linear alcohols, vinyl acetate, alkanes, alpha olefins, various hydrocarbon-based fuels, ethanol and the like. These compounds can then be further processed using methods well known to one of ordinary skill in the art to obtain other valuable chemicals and consumer products.

Embodiments disclosed herein include, but are not limited to:

Embodiment A: A catalyst composition including an oxidative dehydrogenation catalyst including a mixed metal oxide having the empirical formula:

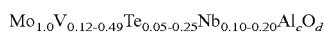

$$Mo_{1.0}V_{0.12-0.49}Te_{0.05-0.25}Nb_{0.10-0.20}Al_cO_d$$

wherein c is from 0 to 2.0, d is a number to satisfy the valence of the oxide, and the composition is at least 40 wt. % amorphous as measured by XRD.

Embodiment A can have one or more of the following additional elements in any combination:

Element A1: Wherein the composition is from 60 wt. % to 80 wt. % amorphous.

Element A2: Wherein the composition further includes an adjuvant.

Element A3: Wherein the composition further includes an adjuvant; and wherein the adjuvant includes about 30 wt. % to about 90 wt. % of the catalyst composition.

Element A4: Wherein the composition further includes an adjuvant; and wherein the adjuvant includes about 60 wt. % of the catalyst composition.

Element A5: Wherein the oxidative dehydrogenation catalyst includes about 10 wt. % to about 70 wt. % of the catalyst composition.

Element A6: Wherein the oxidative dehydrogenation catalyst includes about 40 wt. % of the catalyst composition.

Element A7: Wherein the composition further includes an adjuvant; and wherein the adjuvant includes a support, a binder, an agglomerating agent, a promoter, an agent capable of at least partially reacting with the oxidative dehydrogenation catalyst, or a combination thereof.

Element A8: Wherein the composition further includes an adjuvant; and wherein the adjuvant includes an agent capable of at least partially reacting with the oxidative dehydrogenation catalyst.

Element A9: Wherein the mixed metal oxide has the empirical formula:

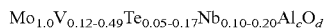

$$Mo_{1.0}V_{0.12-0.49}Te_{0.05-0.17}Nb_{0.10-0.20}Al_cO_d$$

wherein c is 0.01 to 2.0 and d is a number to satisfy the valence of the oxide.

Element A10: Wherein the composition further includes an adjuvant; and wherein the adjuvant includes an alumina.

Element A11: Wherein the composition further includes an adjuvant; and wherein the adjuvant includes an alumina; and wherein the alumina is selected from an aluminum oxide, an alumina monohydrate, an alumina trihydrate, an alumina-silica, a bauxite, a calcined alumina, a transition alumina, a calcined hydrotalcite, or a combination thereof.

Element A12: Wherein the composition further includes an adjuvant; and wherein the adjuvant includes an alumina; and wherein the alumina includes a gibbsite, a bayerite, a boehmite, or a combination thereof.

Element A13: Wherein the composition further includes an adjuvant; and wherein the adjuvant includes an alumina; and wherein the alumina includes a boehmite.

Element A14: Wherein the composition further includes an adjuvant; and wherein the adjuvant includes an alumina; and wherein the alumina includes a boehmite; and wherein the boehmite includes a pseudoboehmite.

Element A15: Wherein the composition further includes an adjuvant; and wherein the adjuvant includes an alumina; and wherein the alumina includes about 30 wt. % to about 90 wt. % of the catalyst composition.

Element A16: Wherein the composition further includes an adjuvant; and wherein the adjuvant includes an alumina; and wherein the alumina includes about 60 wt. % of the catalyst composition.

Element A17: Element A17: Wherein the composition further includes an adjuvant; and wherein the adjuvant includes an alumina; and wherein the molar ratio of molybdenum to vanadium in the catalyst composition is from 1:0.12 to 1:0.49 as determined by PIXE, the molar ratio of molybdenum to tellurium in the catalyst composition is from 1:0.05 to 1:0.25, as determined by PIXE, the molar ratio of molybdenum to niobium in the catalyst composition is from 1:0.10 to 1:0.20, as determined by PIXE, and the molar ratio of molybdenum to aluminum in the catalyst composition is from 0.01 to 2.0, as determined by PIXE.

Element A18: Wherein the composition further includes an adjuvant; and wherein the adjuvant includes an alumina; and wherein the molar ratio of molybdenum to vanadium in the catalyst composition is from 1:0.20 to 1:0.45, as determined by PIXE, the molar ratio of molybdenum to tellurium in the catalyst composition is from 1:0.10 to 1:0.20, as determined by PIXE, the molar ratio of molybdenum to niobium in the catalyst composition is from 1:0.10 to 1:0.20, as determined by PIXE, and the molar ratio of molybdenum to aluminum in the catalyst composition is from 0.05 to 0.5, as determined by PIXE.

Element A19: Wherein the composition further includes an adjuvant; and wherein the adjuvant includes an alumina; and wherein the molar ratio of molybdenum to vanadium in the catalyst composition is from 1:0.30 to 1:0.45, as determined by PIXE, the molar ratio of molybdenum to tellurium in the catalyst composition is from 1:0.12 to 1:0.18, as determined by PIXE, the molar ratio of molybdenum to niobium in the catalyst composition is from 1:0.12 to 1:0.18, as determined by PIXE, and the molar ratio of molybdenum to aluminum in the catalyst composition is from 0.10 to 0.30, as determined by PIXE.

Element A20: Wherein the catalyst composition is characterized by having XRD diffraction peaks (2θ degrees) at least at 22±0.2, 27±0.2, 28.0±0.2, and 28.3±0.2, wherein the XRD is obtained using CuKα radiation.

Element A21: Wherein the catalyst composition has a 35% conversion temperature of about 340° C. to about 390° C.

Element A22: Wherein the catalyst composition has a 35% conversion temperature of about 350° C. to about 370° C.

Element A23: Wherein the catalyst composition has a selectivity to ethylene of greater than about 90%.

Element A24: Wherein the catalyst composition has a selectivity to ethylene of greater than about 93%.

Element A25: Wherein the catalyst composition has a 35% conversion temperature of about 350° C. to about 390° C. and a selectivity to ethylene of greater than about 90%.

Element A26: Wherein the catalyst composition has a 35% conversion temperature of about 360° C. to about 370° C. and a selectivity to ethylene of greater than about 93%.

By way of non-limiting example, exemplary element combinations applicable to Embodiment A include: A1 and A2; A1, A2, and A10; A13 and A17; A13, A17, and A20; and the like.

Embodiment B: A catalyst composition including a boehmite and an oxidative dehydrogenation catalyst including a mixed metal oxide having the empirical formula:

$$Mo_{1.0}V_{0.12-0.49}Te_{0.05-0.25}Nb_{0.10-0.20}Al_{0-2.0}O_d$$

wherein d is a number to satisfy the valence of the oxide, the boehmite includes about 50 wt. % to about 70 wt. % of the catalyst composition, the oxidative dehydrogenation catalyst includes about 30 wt. % to about 50 wt. % of the catalyst composition, and the composition is about 60 wt. % to about 80 wt. % amorphous as measured by XRD.

Embodiment B can have the following additional element:

Element B1: Wherein the catalyst composition has a 35% conversion temperature of about 350° C. to about 370° C. and a selectivity to ethylene of greater than about 90%.

Embodiment C: A catalyst composition including an alumina and an oxidative dehydrogenation catalyst including a mixed metal oxide having the empirical formula:

$$Mo_{1.0}V_{0.12-0.49}Te_{0.05-0.25}Nb_{0.10-0.20}Al_{0-2.0}O_d$$

wherein d is a number to satisfy the valence of the oxide, and the catalyst composition is at least 40 wt. % amorphous as measured by XRD.

Embodiment C can have one or more of the following additional elements in any combination:

Element C1: Wherein the composition is prepared by a method including providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition.

Element C2: Wherein the composition is prepared by a method including providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the water is selected from distilled water, deionized water, demineralized water, mineral water, or a combination thereof.

Element C3: Wherein the composition is prepared by a method including providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the water includes distilled water.

Element C4: Wherein the composition is prepared by a method including providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the water includes about 10 wt. % to about 99 wt. % of the mixture.

Element C5: Wherein the composition is prepared by a method including providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the water includes about 40 wt. % to about 60 wt. % of the mixture.

Element C6: Wherein the composition is prepared by a method including providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the pre-calcination catalyst composition is calcined at a temperature of about 300° C. to about 450° C.

Element C7: Wherein the composition is prepared by a method including providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the pre-calcination catalyst composition is calcined at a temperature of about 325° C. to about 375° C.

Element C8: Wherein the composition is prepared by a method including providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the pre-calcination catalyst composition is calcined at a temperature of about 350° C.

Element C9: Wherein the composition is prepared by a method including providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the mixture including the oxidative dehydrogenation catalyst precursor, the alumina, and the water is heated at a temperature of about 60° C. to about 100° C. to remove at least 40% of the water.

Element C10: Wherein the composition is prepared by a method including providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the mixture including the oxidative dehydrogenation catalyst precursor, the alumina, and the water is heated at a temperature of about 70° C. to about 90° C. to remove at least 40% of the water.

Element C11: Wherein the composition is prepared by a method including providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the mixture including the oxidative dehydrogenation catalyst precursor, the alumina, and the water is heated at a temperature of about 80° C. to remove at least 40% of the water.

By way of non-limiting example, exemplary element combinations applicable to Embodiment C include: C1 and C9; C1 and C10; and the like.

Embodiment D: A method of preparing a catalyst composition that includes an alumina and an oxidative dehydrogenation catalyst including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide; wherein the method includes: providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}Al_{0-2.0}O_d$$

wherein d is a number to satisfy the valence of the oxide; heating the mixture including the oxidative dehydrogenation catalyst precursor, the alumina, and the water to remove at least 40 wt. % of the water to provide a pre-calcination catalyst composition; and calcining the pre-calcination catalyst composition to provide the catalyst composition.

Embodiment D can have one or more of the following additional elements in any combination:

Element D1: Wherein the mixture includes about 20 wt. % to about 90 wt. % of the water, about 5 wt. % to about 50 wt. % of the oxidative dehydrogenation catalyst, and about 5 wt. % to about 30 wt. % of the alumina.

Element D2: Wherein the mixture includes about 40 wt. % to about 60 wt. % of the water, about 25 wt. % to about 35 wt. % of the mixed metal oxide catalyst, and about 15 wt. % to about 25 wt. % of the alumina.

Element D3: Wherein the mixture is heated at a temperature of about 60° C. to about 100° C.

Element D4: Wherein the mixture is heated at a temperature of about 70° C. to about 90° C.

Element D5: Wherein the mixture is heated at a temperature of about 80° C.

Element D6: Wherein heating the mixture removes about 50 wt. % to about 99.9 wt. % of the water.

Element D7: Wherein the calcination temperature is about 300° C. to about 450° C.

Element D8: Wherein the calcination temperature is about 325° C. to about 375° C.

Element D9: Wherein the calcination temperature is about 350° C.

Element D10: Wherein the calcination time is about 1 hour to about 48 hours.

Element D11: Wherein the calcination time is about 1 hour to about 12 hours.

Element D12: Wherein the calcination time is about 1 hour to about 4 hours.

Element D13: Wherein the calcination time is about 2 hours.

Element D14: Wherein the calcination temperature is about 300° C. to about 450° C. and the calcination time is about 1 hour to about 48 hours.

Element D15: Wherein the calcination temperature is about 325° C. to about 375° C. and the calcination time is about 1 hour to about 4 hours.

Element D16: Wherein the calcination temperature is about 350° C. to and the calcination time is about 2 hours.

Element D17: Wherein the amorphous content of the catalyst composition is greater than the predicted additive amorphous content for the catalyst composition.

By way of non-limiting example, exemplary element combinations applicable to Embodiment D include: D1 and D3; D1, D3 and D17; and the like. Embodiment E: A method of increasing the amorphous phase of a catalyst composition including an oxidative dehydrogenation catalyst including a mixed metal oxide having the empirical formula:

$$Mo_{1.0}V_{0.12-0.49}Te_{0.05-0.25}Nb_{0.10-0.20}Al_cO_d$$

wherein c is from 0 to 2.0 and d is a number to satisfy the valence of the oxide, the method including: providing a mixture including the oxidative dehydrogenation catalyst, an alumina, and a water; heating the mixture including the oxidative dehydrogenation catalyst, the alumina, and the water to remove at least 40 wt. % of the water to provide a pre-calcination catalyst composition; and calcining the pre-calcination catalyst composition to provide the catalyst composition.

Embodiment F: A catalyst composition including molybdenum, vanadium, tellurium, niobium, aluminum and oxygen, wherein: the molar ratio of molybdenum to vanadium is from 1:0.12 to 1:0.49, as determined by PIXE; the molar ratio of molybdenum to tellurium is from 1:0.05 to 1:0.25, as determined by PIXE; the molar ratio of molybdenum to niobium is from 1:0.10 to 1:0.20, as determined by PIXE; the molar ratio of molybdenum to aluminum is from 0.01 to 2.0, as determined by PIXE; oxygen is present at least in an amount to satisfy the valency of any present metal oxides; and the composition is at least 40 wt. % amorphous as measured by XRD.

Embodiment F can have one or more of the following additional elements in any combination:

Element F1: Wherein the molar ratio of molybdenum to vanadium is from 1:0.20 to 1:0.45, as determined by PIXE, the molar ratio of molybdenum to tellurium is from 1:0.10 to 1:0.20, as determined by PIXE, the molar ratio of molybdenum to niobium is from 1:0.10 to 1:0.20, as determined by PIXE, and the molar ratio of molybdenum to aluminum is from 0.05 to 0.5, as determined by PIXE.

Element F2: Wherein the molar ratio of molybdenum to vanadium is from 1:0.30 to 1:0.45, the molar ratio of molybdenum to tellurium is from 1:0.12 to 1:0.18, as determined by PIXE, the molar ratio of molybdenum to niobium is from 1:0.12 to 1:0.18, as determined by PIXE, and the molar ratio of molybdenum to aluminum is from 0.10 to 0.30, as determined by PIXE.

Element F3: Wherein the composition is from 60 wt. % to 80 wt. % amorphous.

Element F4: Wherein the source of aluminum in the catalyst composition includes a boehmite.

Element F5: Wherein the catalyst composition is characterized by having XRD diffraction peaks (2θ degrees) at least at 22±0.2, 27±0.2, 28.0±0.2, and 28.3±0.2, wherein the XRD is obtained using CuKα radiation.

Element F6: Wherein the catalyst composition has a 35% conversion temperature of about 340° C. to about 390° C.

Element F7: Wherein the catalyst composition has a 35% conversion temperature of about 350° C. to about 370° C.

Element F8: Wherein the catalyst composition has a selectivity to ethylene of greater than about 90%.

Element F9: Wherein the catalyst composition has a selectivity to ethylene of greater than about 93%.

Element F10: Wherein the catalyst composition has a 35% conversion temperature of about 350° C. to about 390° C. and a selectivity to ethylene of greater than about 90%.

Element F11: Wherein the catalyst composition has a 35% conversion temperature of about 360° C. to about 370° C. and a selectivity to ethylene of greater than about 93%.

Element F12: Wherein the catalyst composition is prepared by a method that includes providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition.

Element F13: Wherein the catalyst composition is prepared by a method that includes providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the water is selected from distilled water, deionized water, demineralized water, mineral water, or a combination thereof.

Element F14: Wherein the catalyst composition is prepared by a method that includes providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the water includes distilled water.

Element F15: Wherein the catalyst composition is prepared by a method that includes providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the water includes about 10 wt. % to about 99 wt. % of the mixture.

Element F16: Wherein the catalyst composition is prepared by a method that includes providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the water includes about 40 wt. % to about 60 wt. % of the mixture.

Element F17: Wherein the catalyst composition is prepared by a method that includes providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the pre-calcination catalyst composition is calcined at a temperature of about 300° C. to about 450° C.

Element F18: Wherein the catalyst composition is prepared by a method that includes providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the pre-calcination catalyst composition is calcined at a temperature of about 325° C. to about 375° C.

Element F19: Wherein the catalyst composition is prepared by a method that includes providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the pre-calcination catalyst composition is calcined at a temperature of about 350° C.

Element F20: Wherein the catalyst composition is prepared by a method that includes providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the mixture including the oxidative dehydrogenation catalyst precursor, the alumina, and the water is heated at a temperature of about 60° C. to about 100° C. to remove at least 40% of the water.

Element F21: Wherein the catalyst composition is prepared by a method that includes providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the mixture including the oxidative dehydrogenation catalyst precursor, the alumina, and the water is heated at a temperature of about 70° C. to about 90° C. to remove at least 40% of the water.

Element F22: Wherein the catalyst composition is prepared by a method that includes providing a mixture including the alumina, a water, and an oxidative dehydrogenation catalyst precursor including a mixed metal oxide having the empirical formula:

$$Mo_{1.0}V_{0.12-0.49}Te_{0.05-0.25}Nb_{0.10-0.20}O_d$$

wherein d is a number to satisfy the valence of the oxide, removing at least 40 wt. % of the water from the mixture to provide a pre-calcination catalyst composition, and calcining the pre-calcination catalyst composition to provide the catalyst composition; and wherein the mixture including the oxidative dehydrogenation catalyst precursor, the alumina, and the water is heated at a temperature of about 80° C. to remove at least 40% of the water.

By way of non-limiting example, exemplary element combinations applicable to Embodiment F include: F1 and F3; F3 and F4; F3 and F5; F3, F5, and F12; F3, F5, F12, and F20; and the like.

EXAMPLES

Example 1.1

$(NH_4)_6Mo_6TeO_{24} \cdot 7H_2O$ (96.1334 grams (g)) was weighed into a 2 liter (L) round bottom flask with 300 milliliters (mL) of distilled water and the mixture was stirred at 300 rotations per minute (rpm) and heated with a warm water bath controlled to a temperature of 60° C. for 30 minutes to dissolved the salt. $VOSO_4 \cdot 3.35H_2O$ (70.0861 g) was weighed into a 400 mL beaker along with 100 mL of distilled water the mixture was stirred at 300 rpm and heated with a warm water bath controlled to a temperature of 60° C. for 30 minutes to dissolved the salt. The warm blue solution of $VOSO_4 \cdot 3.41 H_2O$ was added to the warm turbid mixture of $(NH_4)_6Mo_6TeO_2 \cdot H_2O$ dropwise in air through a dropper funnel over 27 minutes to form a clear black/purple solution. The resulting black/purple solution was mixed at 300 rpm for approximately 1 hour (h). To the resulting black solution, a room temperature $H_3[NbO(C_2O_4)_3]$ (192.20 g (0.356 mmol$_{Nb}$/g$_{soln}$)) was added dropwise with a dropper funnel to form a purple slurry. The purple slurry was added to a 2L PARR autoclave containing a large Teflon stir bar. The autoclave was sealed and the air atmosphere inside was purged via 10 cycles of 15 psig nitrogen followed by full vacuum. The 2L PARR autoclave was left under 15 psig nitrogen and sealed. The 2L PARR autoclave was connected to a back-pressure regulator and condenser setup. The reactor contents were left to stir overnight via magnetic stir plate/Teflon stir bar. The stir plate was set at 300 rpm.

The next day the 2L reactor, back pressure regulator, and condenser setup were purged with the 15 psig nitrogen. The backpressure regulator was dialed to 160 psig during the nitrogen purge step. The contents of the reactor were set to stir using either a magnetic stir rod with a stir plate or an overhead agitator assembly. The reactor was heated to an internal temperature of 172-175° C. using a fitted heating jacket, the reaction was heated for 24 hours.

The next day the pressure in the 2 L reactor was released and the purple product slurry from the reactor was filtered through Buchner funnel (using Whatman Filter Paper—1 Qualitative. 24 cm diameter. Cat No 1001 240. 11 µm porosity) using vacuum. Resulting purple powder was washed with distilled water and filtered until filtrate ran clear (approximately 200 mL of distilled water). Filter cake from the catalyst was dried at 90° C. using a vacuum oven (full vacuum) throughout the day. At the end of the day, the oven temperature was turned off and the filter cake sat under static vacuum at room temperature over the weekend. After the weekend, the catalyst was further dried in a convention oven at 90° C. throughout the day and overnight. The dried product was ground using a blender and this powder material was Pre-catalyst 1.1, which was carried forward for calcination procedure.

Pre-catalyst 1.1 was loaded in 30 to 40 g portions into 4 boats onto quartz tube reactor (QRU). The QRU was purged under bulk nitrogen for at least 8 hours and then switched to 400 standard cubic centimeters per minute (sccm) purified nitrogen (bulk nitrogen passed through catalyst beds). After the furnace was turned on, a heating program of a temperature ramp up to 600° C. in 6 hours was employed and the 600° C. temperature was held for 2 hours to yield Catalyst 1.1 as a black solid product.

Example 2.1

The procedure of Example 1.1 was repeated to yield Catalyst 2.1.

Example 2.2

To a 100 mL beaker was charged 6.0097 g VERSAL® 250 Alumina (60 wt. %). To a weigh boat was charged 40 wt % of an oxidative dehydrogenation catalyst having the empirical formula $Mo_{1.0}V_{0.12-0.49}Te_{0.05-0.17}Nb_{0.10-0.20}O_d$ and 4.0043 g. To the beaker was charged 10 mL of distilled water. To the beaker containing the VERSAL® 250 Alumina and the oxidative dehydrogenation catalyst was charged 0.5224 g of 1 molar (M) phosphoric acid. Using a glass agitator shaft and a 1" Teflon stir blade, the overhead agitator was to set to 100 rpm and the beaker was placed on a hot plate set to 70° C. The solution was slowly evaporated on the hot plate to form a paste (approximately 25 minutes). The black/purple paste was then dried in the oven overnight at 90° C. The resulting dried black/purple paste inside the 100 mL beaker was transferred the to muffle furnace and calcined at 350° C. for 2 h (with a ramp time 30 minutes) to yield Catalyst Composition 2.2.

Example 2.3

41 wt. % of an oxidative dehydrogenation catalyst having the empirical formula $Mo_{1.0}V_{0.12-0.49}Te_{0.05-0.17}Nb_{0.10-0.20}O_d$ was mixed with VERSAL® 250 Alumina (59 wt. %) as dry powders in an 18" Lancaster mix muller. Nitric acid was used as the alumina peptizing agent at a level of 0.001-0.2 g $HNO_3$/g mixed powder until a consistency for extrusion was reached. The extruded catalyst was ground using a mortar and pestle to yield Catalyst Composition 2.3.

Example 2.4

To a beaker was charged 4 g of Catalyst 2.1 and 6 g of VERSAL® 250 Alumina. The two powders were mixed together to obtain a consistent mixture. This mixture was then pressed to yield Catalyst Composition 2.4.

Example 2.5

The 25% conversion temperatures and selectivity of Catalyst Compositions 2.1-2.4 were determined. The 25% conversion temperature was determined in a similar fashion as the 35% conversion temperature, as described herein, with linear equation for ethane conversion being solved to determine the temperature in which the ethane conversion is 25. The feed gas included ethane and oxygen having a molar ration of 82% Ethane and 18% Oxygen. The flow rate of the feed gas was about 75 sccm.

The 25% conversion temperatures and selectivity of Catalyst 2.1 and Catalyst Compositions 2.2-2.4 are presented in Table 1.

TABLE 1

| Material | 25% Conversion Temperature (° C.) | Selectivity (%) |
|---|---|---|
| Catalyst 2.1 | 375.41 | 97.37 |
| Catalyst Composition 2.2 | 356.91 | 96.58 |
| Catalyst Composition 2.3 | 362 | 94.58 |
| Catalyst Composition 2.4 | 400 | 90.00 |

Example 2.6

Figure 2:
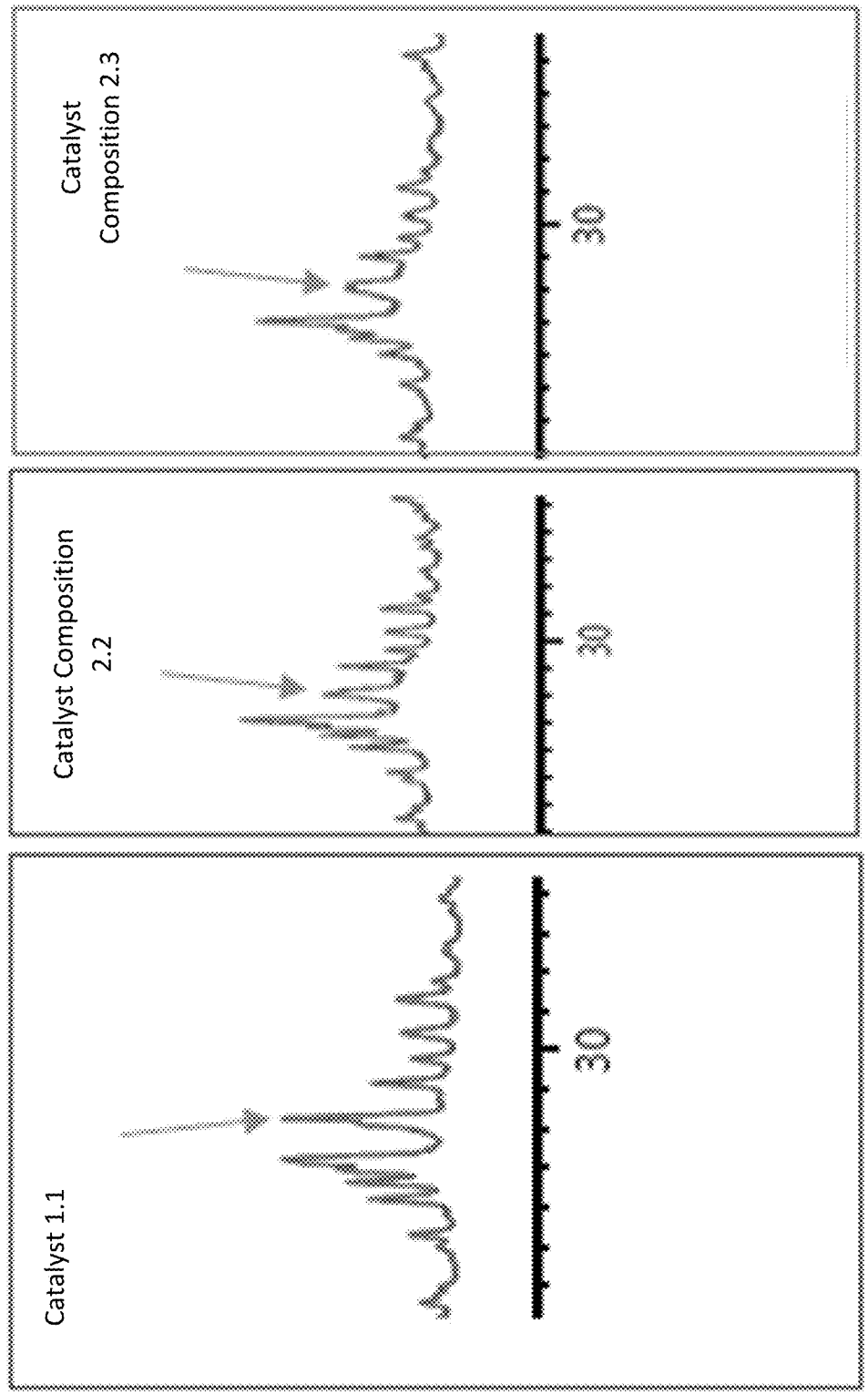
FIG. 2 shows the XRD patterns for the Catalyst 1.1, Catalyst Composition 1.2, and Catalyst Composition 2.3.

The XRD patterns for the Catalyst 2.1 and Catalyst Compositions of 2.2-2.4 were then obtained and are shown in FIG. 2.

An examination of the XRD patterns indicated that the peak at 28.04° 2θ was significantly more intense as compared to the peak at 28.32 2θ°. In the case of Catalyst Composition 2.2 the peak at 28.32° 2θ can be seen as a barely distinguishable peak shoulder. Whereas for Catalyst 1.1, one can clearly see that the peak at 28.32° 2θ dominates the double peak. The XRD Catalyst 2.1 had peaks at 28° two-theta where a single peak exists. In the case with the catalyst alumina mixture an additional smaller peak appeared at 27.5° two-theta. In addition, for the extruded catalyst, these two peaks were no longer skewed to either side and are instead even in intensity. The addition of water during these processing steps not only seems to be important for proper mixing but it also seems to change the composition of the resulting catalyst mixture.

Example 3.1

4.01 g of Catalyst 1.1 and 6.0079 g of CATAPAL® B alumina binder were added to a 100 mL beaker and 10 mL of distilled water was added to create a suspension. The stirred suspension was evaporated using a hot plate. The beaker was placed directly on the hot plate with the thermocouple hovering just above the hot plate. The thermocoupled temperature was set to 70° C. The hot plate temperature was not determined. When the evaporation of the suspension produced a paste, the resulting paste (still in 100 mL glass beaker) was transferred to an oven. The time it took for the water to evaporate from the catalyst mixture was approximately 30 minutes producing a purple paste like substance. The paste was then dried in the oven at 90° C. overnight. The ramp time was 1 hour to reach 90° C. from 23° C. (room temperature). In the morning, the dried paste (still in 100 mL glass beaker) was removed from the 90° C. oven and transferred to a muffle furnace. The muffle furnace was heated at 350° C. for 2 hours with a ramp rate of approximately 30 minutes from room temperature (23° C.) to 350° C. After allowing the furnace to cool, the finished product was pressed on a manual Carver Press to 12 tons, and subsequently crushed and sieved to ensure a final particle size of 425-1000 microns to yield Catalyst Composition 3.1. Catalyst Composition 3.1 was screened on MRU as disclosed herein and the results are presented in Table 3.

Further, an SEM images of Catalyst Composition 3.1, which are shown in FIGS. 1A and 1B.

Example 3.2

To a 100 mL beaker was charged 4 g of Catalyst 1.1 and 6 g of flash calcined alumina. To this mixture was added 17 mL of distilled water to give a slurry. The slurry was stirred using an overhead agitator with a glass stir shaft and 1" TEFLON® stir blade. The slurry was heated to 80-100° C. to remove enough water to form a paste. The paste was dried at 90° C. in an oven overnight and calcined in a muffle furnace at 350° C. for 2 hours with a 30-minute ramp time to yield Catalyst Composition 3.2.

Example 3.3

To a 100 mL beaker was charged 4 g of Catalyst 1.1 and 6 g of VERSAL® 250 Alumina. To this mixture was added 15 mL of distilled water to give a slurry. The slurry was stirred using an overhead agitator with a glass stir shaft and 1" TEFLON® stir blade. The slurry was heated to 80-100° C. to remove enough water to form a paste. The paste was dried at 90° C. in an oven overnight and calcined in a muffle furnace at 350° C. for 2 hours with a 30-minute ramp time to yield Catalyst Composition 3.3.

Example 3.4

To a 100 mL beaker was charged 4 g of Catalyst 1.1 and 6 g of Catalyst 1.1. To this mixture was added 15 mL of distilled water to give a slurry. The slurry was stirred using an overhead agitator with a glass stir shaft and 1" TEFLON® stir blade. The slurry was heated to 80-100° C. to remove enough water to form a paste. The paste was dried at 90° C. in an oven overnight and calcined in a muffle furnace at 500° C. for 2 hours with a 30-minute ramp time to yield Catalyst Composition 3.4.

Example 3.5

An oxidative dehydrogenation catalyst was prepared having the empirical formula $Mo_{1.0}V_{0.32-0.49}Te_{0.10-0.17}Nb_{0.14-0.17}O_d$. The catalyst was prepared by the same method as Catalyst 1.1 and extruded externally into pelletized extrudates, to yield Catalyst 3.5.

Example 3.6

Catalyst Composition 3.6 was prepared having the empirical formula $Mo_{1.0}V_{0.12-0.49}Te_{0.05-0.17}Nb_{0.14-0.17}Al_{0.77-0.87}O_d$. The catalyst composition was prepared by mixing a catalyst prepared similarly to Catalyst 1.1 and an alumina by an extrusion process in order to form pelletized extrudates.

Example 3.7

To a 100 mL beaker was charged 4.0322 g of Catalyst 1.1, 6.0074 g of CATAPAL® B alumina (SASOL) and 10 mL of distilled water. The beaker was clamped into an oil bath and an overhead agitator was set up with a glass stir shaft and 0.5" Teflon stir blade to mix the light purple aqueous. The oil bath was set to 100° C. and the overhead agitator was set to 100 rpm. The aqueous mixture was stirred and heated for 55 minutes. After which, the paste-like mixture was heated in an oven at 90° C. for 18 hours. Following this, the light purple powder was calcined in a muffle furnace at 350° C. for 2 hours with a 30 minute ramp time to yield Catalyst Composition 3.7 which was submitted for PIXE testing.

Example 3.8

To a 100 mL beaker was charged 4.04 g of Catalyst 1.1, 6.03 g of CATAPAL® B alumina (SASOL) and 10 mL of distilled water. The beaker was clamped into an oil bath and an overhead agitator was assembled using a glass stir shaft and a 0.5" Teflon stir blade. The agitator was set to 100 rpm and the oil bath was set to 100° C. The aqueous mixture was stirred at 100° C. at 100 rpm for 1 hour. Subsequently, the light purple paste was dried in a 90° C. oven for 18 hours. Afterwards the light purple powder was calcined in a muffle furnace at 500° C. for 2 hours with a ramp time of 30 minutes to yield Catalyst Composition 3.8, which was submitted PIXE testing.

Example 3.9

The 35% conversion temperature and selectivity of Catalyst 1.1 and Catalyst Compositions 3.2-3.6 were determined using an MRU as described herein. The feed gas composition entering the reactor tube 35% ethane, 17.5% oxygen, 47.5% nitrogen (molar ratio). The WHSV based on the active phase was 2.97 $h^{-1}$. The flow rate of the feed gas was about 74.6 sccm. The 35% conversion temperature and selectivity of Catalyst 1.1 and Catalyst Compositions 3.2-3.6 are presented in Table 3.

TABLE 3

| Material | 35% Conversion Temperature (° C.) | Selectivity (%) |
|---|---|---|
| Catalyst 1.1 | 365.81 | 97.30 |
| Catalyst Composition 3.2 | 392.43 | 91.77 |
| Catalyst Composition 3.3 | 355.50 | 95.63 |
| Catalyst Composition 3.4 | 365 | 90 |
| Catalyst 3.5 | 375 | 95 |
| Catalyst Composition 3.6 | 380 | 90 |

Example 3.10

The amorphous content of Catalyst 1.1, flash calcined alumina, and boehmite (VERSAL® 250) was determined by XRD. Subsequently, the predicted additive amorphous content was calculated based on the determined amorphous content of Catalyst 1.1, flash calcined alumina, and boehmite and the weight percent Catalyst 1.1, flash calcined alumina, and boehmite in the compositions. For example, the predicted additive amorphous content of Catalyst Composition 3.3 was calculated to be 47.72% as follows because the composition contained 60 wt. % of 51.2% amorphous boehmite and 40 wt. % of 42.5% amorphous Catalyst 1.1 (0.6×51.2+0.4×42.5=47.72%). The actual amorphous content of Catalyst Compositions 3.2-3.6 was then determined to by XRD. These calculations and results are shown in Table 4.

TABLE 4

| Material | Amorphous content (wt. %) | Predicted additive amorphous content (wt. %) | Amorphous content of catalyst (wt. %) | Amorphous content of alumina (wt. %) |
|---|---|---|---|---|
| Catalyst 1.1 | 42.5 | | | |
| Boehmite (VERSAL ® 250) | 51.2 | | | |
| Flash Calcined Alumina | 92.1 | | | |
| Catalyst Composition 3.2 | 57.7 | 72.26 | 0.0 | 98.7 |
| Catalyst Composition 3.3 | 74.2 | 47.72 | 37 | 99 |
| Catalyst Composition 3.4 | 60 | 47.72 | 0.0 | 100 |
| Catalyst 3.5 | 24 | | | |
| Catalyst Composition 3.6 | 58.8 | 38.96 | 15.25 | 86.73 |

Surprisingly, when a catalyst composition is prepared as disclosed in Example 3.3 (e.g., Catalyst Composition 3.3), the amorphous content is greater than expected. Moreover, when a catalyst composition is prepared as disclosed in Example 3.3, the catalyst composition a lower 35% conversion temperature and comparable selectivity when compared to the oxidative dehydrogenation catalyst by itself—as can be seen by comparing the 35% conversion temperature and selectivity for Catalyst 1.1 and Catalyst Composition 3.3.

Separately, as can be seen for Catalyst Composition 3.2, the addition of flash calcined alumina to Catalyst 1.1 resulted in an amorphous content that was less than predicted. This suggests that the addition of flash calcined alumina promotes the crystallization in the catalyst composition.

As discussed above, extruded Catalyst Composition 3.6 differs, in part, from Catalyst Composition 3.3 in the amount of water added to the mixture of oxidative dehydrogenation catalyst and alumina. Specifically, less than 10 wt. % of water was added during the preparation of Catalyst Composition 3.6 versus approximately 50 wt. % water in Catalyst Composition 3.3. Additionally, the extrusion step was followed by drying and calcining at 350° C. It can be seen procedure for Catalyst Composition 3.6 resulted in a slight increase in the amorphous content in the alumina portion of the catalyst composition and a decrease in the in the amorphous content of the oxidative dehydrogenation catalyst. Further, Catalyst Composition 3.6 had a slight increase in the 35% conversion temperature and a noticeable decrease in selectivity toward ethylene.

Example 3.11

The PIXIE analysis of Catalyst Compositions 3.1, 3.2, 3.7, and 3.8 is presented in Table 5.

TABLE 5

| Sample | Elemental Formula by PIXIE |
|---|---|
| Catalyst Composition 3.1 | $Mo_1V_{0.38}Te_{0.15}Nb_{0.15}Al_{0.19}O_{26.22}$ |
| Catalyst Composition 3.7 | $Mo_1V_{0.36}Te_{0.17}Nb_{0.15}Al_{0.17}O_{28.71}$ |
| Catalyst Composition 3.8 | $Mo_1V_{0.36}Te_{0.16}Nb_{0.16}Al_{0.15}O_{27.75}$ |
| Catalyst Composition 3.2 | $Mo_1V_{0.37}Te_{0.16}Nb_{0.16}Al_{0.16}O_{26.01}$ |
| Catalyst Composition 3.1[a] | $Mo_1V_{0.37}Te_{0.15}Nb_{0.15}Al_{0.14}O_{30.41}$ |
| Catalyst Composition 3.7[b] | $Mo_1V_{0.34}Te_{0.16}Nb_{0.15}Al_{0.16}O_{27.79}$ |

[a]Re-run of the sample Catalyst Composition 3.1.
[b]Re-run of the sample Catalyst Composition 3.7.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of preparing a catalyst composition comprising providing a mixture comprising alumina, water, and an oxidative dehydrogenation catalyst precursor comprising a mixed metal oxide having the empirical formula:

$$Mo_{1.0}V_{0.12-0.49}Te_{0.05-0.25}Nb_{0.10-0.20}O_d$$

heating the mixture comprising the oxidative dehydrogenation catalyst precursor, the alumina, and the water to remove at least 40 wt. % of the water to provide a pre-calcination catalyst composition, and calcining the pre-calcination catalyst composition to provide the catalyst composition having the empirical formula:

$$Mo_{1.0}V_{0.12-0.49}Te_{0.05-0.25}Nb_{0.10-0.20}Al_{0.01-2.0}O_d$$

wherein d is a number to satisfy the valence of the oxide, wherein the catalyst composition is from 60 wt. % to 80 wt. % amorphous.

2. The method of claim 1, wherein the mixture comprises:
about 20 wt. % to about 90 wt. % of the water,
about 5 wt. % to about 50 wt. % of the oxidative dehydrogenation catalyst precursor, and
about 5 wt. % to about 30 wt. % of the alumina.

3. The method of claim 1, wherein the mixture is heated at a temperature of about 60° C. to about 100° C.

4. The method of claim 1, wherein heating the mixture removes about 50 wt. % to about 99.9 wt. % of the water.

5. The method of claim 1, wherein the calcination temperature is about 300° ° C. to about 450° C.

6. The method of claim 1, wherein the catalyst composition has an amorphous content of 5 wt. % to 50 wt. % greater than the predicted additive amorphous content for the catalyst composition.

7. A method of claim 1, wherein the catalyst composition has the empirical formula:

$$Mo_{1.0}V_{0.12-0.49}Te_{0.05-0.25}Nb_{0.10-0.20}Al_{0.5-2.0}O_d$$

wherein d is a number to satisfy the valence of the oxide.

8. A method of claim 1, wherein the catalyst composition has a molar ratio of molybdenum to vanadium from 1:0.12 to 1:0.49, as determined by particle-induced X-ray emission (PIXE).

9. A method of claim 1, wherein the catalyst composition has a molar ratio of molybdenum to tellurium is from 1:0.05 to 1:0.25, as determined by PIXE.

10. A method of claim 1, wherein the catalyst composition has a molar ratio of molybdenum to niobium is 15 from 1:0.10 to 1:0.20, as determined by PIXE.

11. A method of claim 1, wherein the catalyst composition has a molar ratio of molybdenum to aluminum is from 0.01 to 2.0, as determined by PIXE.

12. A method of increasing the amorphous phase of a catalyst composition comprising an oxidative dehydrogenation catalyst comprising providing a mixture comprising the oxidative dehydrogenation catalyst, alumina, and water, heating the mixture comprising the oxidative dehydrogenation catalyst, the alumina, and the water to remove at least 40 wt. % of the water to provide a pre-calcination catalyst composition, and calcining the pre-calcination catalyst composition to provide the catalyst composition having the empirical formula:

$$Mo_{1.0}V_{0.12-0.49}Te_{0.05-0.25}Nb_{0.10-0.20}Al_{0.1-2.0}O_d$$

wherein d is a number to satisfy the valence of the oxide wherein the catalyst composition is from 60 wt. % to 80 wt. % amorphous.

13. A method of claim 12, wherein the catalyst composition has a molar ratio of molybdenum to vanadium from 1:0.12 to 1:0.49, as determined by PIXE.

14. A method of claim 12, wherein the catalyst composition has a molar ratio of molybdenum to tellurium is from 1:0.05 to 1:0.25, as determined by PIXE.

15. A method of claim 12, wherein the catalyst composition has a molar ratio of molybdenum to niobium is 15 from 1:0.10 to 1:0.20, as determined by PIXE.

16. A method of claim 12, wherein the catalyst composition has a molar ratio of molybdenum to aluminum is from 0.01 to 2.0, as determined by PIXE.

17. A method of claim 12, wherein the catalyst composition has the empirical formula:

$$Mo_{1.0}V_{0.12-0.49}Te_{0.05-0.25}Nb_{0.10-0.20}Al_{0.5-2.0}O_d$$

wherein d is a number to satisfy the valence of the oxide.

* * * * *